US012685599B2

(12) United States Patent
Gregerson et al.

(10) Patent No.: US 12,685,599 B2
(45) Date of Patent: *Jul. 21, 2026

(54) METHODS AND SYSTEMS FOR ROBOT-ASSISTED SURGERY

(71) Applicant: Mobius Imaging, LLC, Shirley, MA (US)

(72) Inventors: Eugene Gregerson, Bolton, MA (US); Todd Furlong, Goffstown, NH (US); Scott Coppen, Amesbury, MA (US); Jeff Baker, Goffstown, NH (US); Steve White, Hudson, MA (US); Russell Stanton, Lunenberg, MA (US)

(73) Assignee: Mobius Imaging, LLC, Shirley, MA (US)

( * ) Notice: Subject to any disclaimer, the term of this patent is extended or adjusted under 35 U.S.C. 154(b) by 67 days.

This patent is subject to a terminal disclaimer.

(21) Appl. No.: 18/360,146

(22) Filed: Jul. 27, 2023

(65) Prior Publication Data

US 2023/0363833 A1 Nov. 16, 2023

Related U.S. Application Data

(62) Division of application No. 16/344,720, filed as application No. PCT/US2017/058105 on Oct. 24, 2017, now Pat. No. 11,751,948.

(Continued)

(51) Int. Cl.
A61B 34/20 (2016.01)
A61B 5/00 (2006.01)
(Continued)

(52) U.S. Cl.
CPC .............. *A61B 34/20* (2016.02); *A61B 5/704* (2013.01); *A61B 17/3423* (2013.01);
(Continued)

(58) Field of Classification Search
CPC ............ A61B 17/3421; A61B 17/3423; A61B 2034/2048; A61B 2034/2055;
(Continued)

(56) References Cited

U.S. PATENT DOCUMENTS 5,799,055 A 8/1998 Peshkin et al.
5,921,992 A 7/1999 Costales et al.
(Continued)

FOREIGN PATENT DOCUMENTS

CN 201422918 Y 3/2010
CN 201542641 U 8/2010
(Continued)

OTHER PUBLICATIONS

English language abstract and machine-assisted English translation for CN 101579269 extracted from espacenet.com database on Jan. 9, 2020, 8 pages.

(Continued)

*Primary Examiner* — Michael T Rozanski
(74) *Attorney, Agent, or Firm* — Howard & Howard Attorneys PLLC

(57) ABSTRACT

Methods and systems for performing robot-assisted surgery, including methods for defining a boundary surface for a robotic surgery system, methods for operating a robotic arm in an image-guided surgery system, methods and systems for providing haptic feedback to a user during robot-assisted surgery, and a robotic arm for use in robot-assisted surgery.

11 Claims, 14 Drawing Sheets

Related U.S. Application Data

(60) Provisional application No. 62/412,422, filed on Oct. 25, 2016.

(51) Int. Cl.

| | |
|---|---|
| *A61B 17/34* | (2006.01) |
| *A61B 34/00* | (2016.01) |
| *A61B 34/32* | (2016.01) |
| *A61B 6/03* | (2006.01) |

(52) U.S. Cl.
CPC .............. *A61B 34/32* (2016.02); *A61B 34/76* (2016.02); *A61B 6/032* (2013.01); *A61B 2034/2048* (2016.02); *A61B 2034/2055* (2016.02); *A61B 2034/2057* (2016.02); *A61B 2034/2065* (2016.02); *A61B 2034/2068* (2016.02); *A61B 2034/2072* (2016.02)

(58) Field of Classification Search
CPC .... A61B 2034/2057; A61B 2034/2059; A61B 2034/2065; A61B 2034/2068; A61B 2034/2072; A61B 2090/363; A61B 2090/364; A61B 2090/3762; A61B 2090/3966; A61B 2505/05; A61B 34/20; A61B 34/30; A61B 34/32; A61B 34/74; A61B 34/76; A61B 5/055; A61B 5/1113; A61B 5/1127; A61B 6/032; A61B 6/463; A61B 6/466; B25J 9/1666
See application file for complete search history.

(56) References Cited

U.S. PATENT DOCUMENTS

| | | | |
|---|---|---|---|
| 6,149,592 | A | 11/2000 | Yanof et al. |
| 6,236,875 | B1 | 5/2001 | Bucholz et al. |
| 6,275,725 | B1 | 8/2001 | Cosman |
| 6,533,455 | B2 | 3/2003 | Graumann et al. |
| 6,772,002 | B2 | 8/2004 | Schmidt et al. |
| 6,785,572 | B2 | 8/2004 | Yanof et al. |
| 7,194,120 | B2 | 3/2007 | Wicker et al. |
| 7,251,522 | B2 | 7/2007 | Essenreiter et al. |
| 7,587,235 | B2 | 9/2009 | Wist et al. |
| 7,699,877 | B2 | 4/2010 | Davison |
| 7,722,530 | B2 | 5/2010 | Davison |
| 7,799,036 | B2 | 9/2010 | Davison et al. |
| 8,016,835 | B2 | 9/2011 | Birkmeyer et al. |
| 8,046,054 | B2 | 10/2011 | Kim et al. |
| 8,118,488 | B2 | 2/2012 | Gregerson |
| 8,126,114 | B2 | 2/2012 | Naylor et al. |
| 8,394,144 | B2 | 3/2013 | Zehavi et al. |
| 8,454,583 | B2 | 6/2013 | Perez-Cruet et al. |
| 8,457,790 | B2 | 6/2013 | Blondel et al. |
| 8,509,503 | B2 | 8/2013 | Nahum et al. |
| 8,761,337 | B2 | 6/2014 | Naylor et al. |
| 8,795,188 | B2 | 8/2014 | Maschke |
| 8,974,372 | B2 | 3/2015 | Fell |
| 8,974,460 | B2 | 3/2015 | De la Fuente Klein et al. |
| 9,125,680 | B2 | 9/2015 | Kostrzewski et al. |
| 9,237,861 | B2 | 1/2016 | Nahum et al. |
| 9,259,282 | B2 | 2/2016 | Azizian et al. |
| 9,283,048 | B2 | 3/2016 | Kostrzewski et al. |
| 9,308,050 | B2 | 4/2016 | Kostrzewski et al. |
| 9,545,233 | B2 | 1/2017 | Sirpad et al. |
| 9,550,299 | B2 | 1/2017 | Wolf et al. |
| 9,750,432 | B2 | 9/2017 | Nahum et al. |
| 9,833,292 | B2 | 12/2017 | Kostrzewski et al. |
| 10,004,562 | B2 | 6/2018 | Kostrzewski et al. |
| 10,039,476 | B2 | 8/2018 | Nahum et al. |
| 10,064,682 | B2 | 9/2018 | Azizian et al. |
| 10,076,385 | B2 | 9/2018 | Shoham et al. |
| 10,136,952 | B2 | 11/2018 | Couture et al. |
| 10,159,534 | B2 | 12/2018 | Maillet et al. |
| 10,653,495 | B2 | 5/2020 | Gregerson et al. |
| 11,103,990 | B2 | 8/2021 | Sebring et al. |
| 11,751,948 | B2 * | 9/2023 | Gregerson ............. B25J 9/1666 606/185 |
| 2004/0010190 | A1 | 1/2004 | Shahidi |
| 2007/0156157 | A1 | 7/2007 | Nahum et al. |
| 2007/0270690 | A1 | 11/2007 | Woerlein |
| 2008/0010706 | A1 | 1/2008 | Moses et al. |
| 2012/0071794 | A1 | 3/2012 | Karni |
| 2013/0211423 | A1 | 8/2013 | Blumenkranz et al. |
| 2013/0282023 | A1 | 10/2013 | Burbank et al. |
| 2014/0003572 | A1 | 1/2014 | Gregerson et al. |
| 2014/0139215 | A1 | 5/2014 | Gregerson et al. |
| 2014/0214049 | A1 | 7/2014 | Jeong et al. |
| 2014/0249546 | A1 | 9/2014 | Shvartsberg et al. |
| 2014/0265182 | A1 | 9/2014 | Stanton et al. |
| 2014/0275953 | A1 | 9/2014 | Gregerson et al. |
| 2014/0276943 | A1 | 9/2014 | Bowling et al. |
| 2015/0202009 | A1 | 7/2015 | Nussbaumer et al. |
| 2015/0279084 | A1 | 10/2015 | Deuerling-Zheng et al. |
| 2015/0335480 | A1 | 11/2015 | Alvarez et al. |
| 2015/0366624 | A1 | 12/2015 | Kostrzewski et al. |
| 2015/0366625 | A1 | 12/2015 | Tognaccini et al. |
| 2016/0030117 | A1 | 2/2016 | Mewes |
| 2016/0081754 | A1 | 3/2016 | Kostrzewski et al. |
| 2016/0174914 | A1 | 6/2016 | Lerch et al. |
| 2016/0220320 | A1 | 8/2016 | Crawford et al. |
| 2016/0235492 | A1 | 8/2016 | Morard et al. |
| 2016/0256225 | A1 * | 9/2016 | Crawford ............... A61B 90/98 |
| 2016/0278875 | A1 | 9/2016 | Crawford et al. |
| 2016/0302871 | A1 | 10/2016 | Gregerson et al. |
| 2017/0071691 | A1 | 3/2017 | Crawford et al. |
| 2017/0079727 | A1 | 3/2017 | Crawford et al. |
| 2017/0172669 | A1 | 6/2017 | Berkowitz et al. |
| 2017/0189125 | A1 | 7/2017 | Malackowski |
| 2017/0202540 | A1 | 7/2017 | Shao et al. |
| 2017/0231702 | A1 | 8/2017 | Crawford et al. |
| 2017/0239002 | A1 | 8/2017 | Crawford et al. |
| 2017/0239003 | A1 | 8/2017 | Crawford et al. |
| 2017/0239006 | A1 | 8/2017 | Crawford et al. |
| 2017/0245951 | A1 | 8/2017 | Crawford et al. |
| 2017/0252112 | A1 | 9/2017 | Crawford et al. |
| 2017/0258533 | A1 | 9/2017 | Crawford et al. |
| 2017/0258535 | A1 | 9/2017 | Crawford et al. |
| 2017/0312039 | A1 | 11/2017 | Crawford et al. |
| 2017/0348061 | A1 | 12/2017 | Joshi et al. |
| 2017/0360513 | A1 | 12/2017 | Amiot et al. |
| 2017/0360517 | A1 | 12/2017 | Crawford et al. |
| 2018/0000546 | A1 | 1/2018 | Crawford et al. |
| 2018/0110573 | A1 | 4/2018 | Kostrzewski |
| 2018/0116739 | A1 | 5/2018 | Gogarty et al. |
| 2018/0116740 | A1 | 5/2018 | Gogarty et al. |
| 2018/0125597 | A1 | 5/2018 | Gogarty et al. |
| 2018/0157238 | A1 | 6/2018 | Gogarty et al. |
| 2018/0185113 | A1 | 7/2018 | Gregerson et al. |
| 2018/0207794 | A1 | 7/2018 | Sebring et al. |
| 2018/0221098 | A1 | 8/2018 | Forsyth et al. |
| 2018/0235715 | A1 | 8/2018 | Amiot et al. |
| 2018/0250077 | A1 | 9/2018 | Xu et al. |
| 2018/0256259 | A1 | 9/2018 | Crawford |
| 2018/0271605 | A1 | 9/2018 | Kostrzewski et al. |
| 2018/0346008 | A1 | 12/2018 | Nahum et al. |
| 2019/0000561 | A1 | 1/2019 | Decker et al. |
| 2019/0000569 | A1 | 1/2019 | Crawford et al. |
| 2019/0021795 | A1 | 1/2019 | Crawford et al. |
| 2019/0021799 | A1 | 1/2019 | Crawford et al. |
| 2019/0021800 | A1 | 1/2019 | Crawford et al. |
| 2019/0029759 | A1 | 1/2019 | Mcdonell |
| 2019/0029765 | A1 | 1/2019 | Crawford et al. |
| 2019/0038362 | A1 | 2/2019 | Nash et al. |
| 2019/0053859 | A1 | 2/2019 | Couture et al. |
| 2019/0069961 | A1 | 3/2019 | Smith et al. |
| 2019/0099222 | A1 | 4/2019 | Nahum et al. |
| 2019/0117313 | A1 | 4/2019 | Crawford |
| 2019/0142533 | A1 | 5/2019 | Itkowitz et al. |
| 2019/0239964 | A1 | 8/2019 | LeBoeuf, II et al. |
| 2019/0269467 | A1 | 9/2019 | Forsyth et al. |

(56) References Cited

U.S. PATENT DOCUMENTS

| | | |
|---|---|---|
| 2019/0274765 A1 | 9/2019 | Crawford et al. |
| 2020/0078097 A1 | 3/2020 | Gregerson et al. |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| WO | 2015115809 A1 | 8/2015 |
| WO | 2016062107 A1 | 4/2016 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for CN 101700184 extracted from espacenet.com database on Jan. 9, 2020, 10 pages.

English language abstract and machine-assisted English translation for CN 101853333 extracted from espacenet.com database on Jan. 9, 2020, 9 pages.

English language abstract and machine-assisted English translation for CN 201422918 extracted from espacenet.com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for WO 2015/115809 extracted from espacenet. com database on Jan. 9, 2020, 8 pages.

English language abstract for WO 2016/062107 extracted from espacenet.com database on May 27, 2020, 2 pages.

English language abstract for WO 2017/036340 extracted from espacenet.com database on Jan. 9, 2020, 2 pages.

International Preliminary Report on Patentability and Written Opinion of the International Searching Authority (Chapter 1 of the Patent Cooperation Treaty) for related International Application No. PCT/US2017/058105 dated May 9, 2019.

International Search Report of the International Searching Authority from the Korean Intellectual Property Office in related International Application No. PCT/US2017/058105 dated Feb. 19, 2018.

PAL jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

Related U.S. Appl. No. 15/701,063, filed Sep. 11, 2017.

Written Opinion of the International Searching Authority from the Korean Intellectual Property Office in related International Application No. PCT/US2017/058105 dated Feb. 19, 2018.

* cited by examiner

300

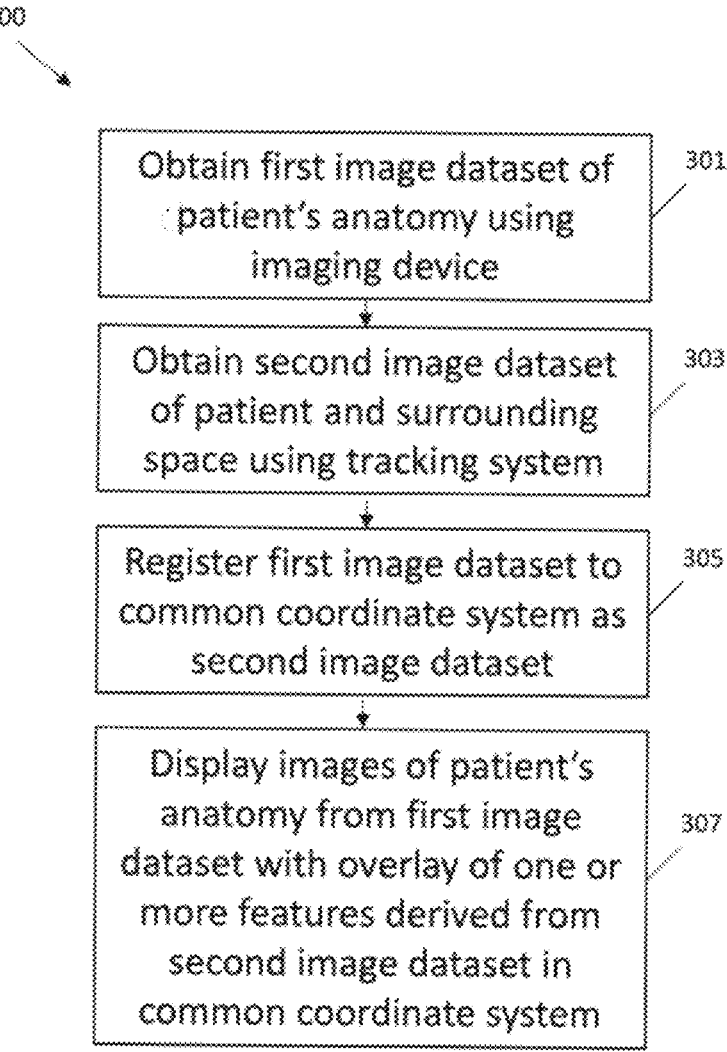

Obtain first image dataset of patient's anatomy using imaging device — 301

Obtain second image dataset of patient and surrounding space using tracking system — 303

Register first image dataset to common coordinate system as second image dataset — 305

Display images of patient's anatomy from first image dataset with overlay of one or more features derived from second image dataset in common coordinate system — 307

FIG. 3

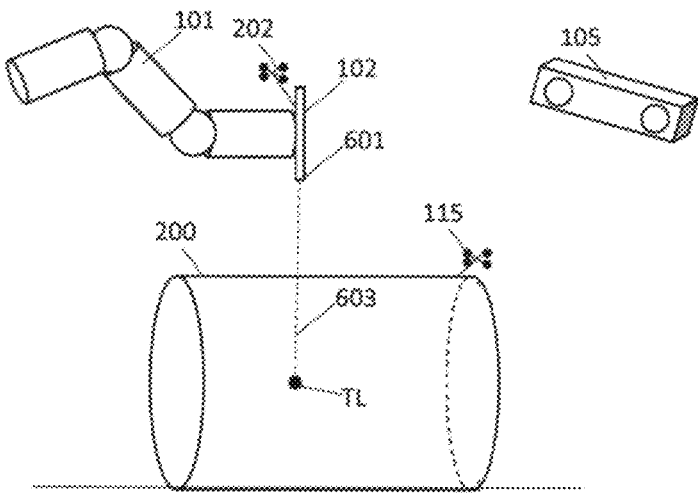
FIG. 6A
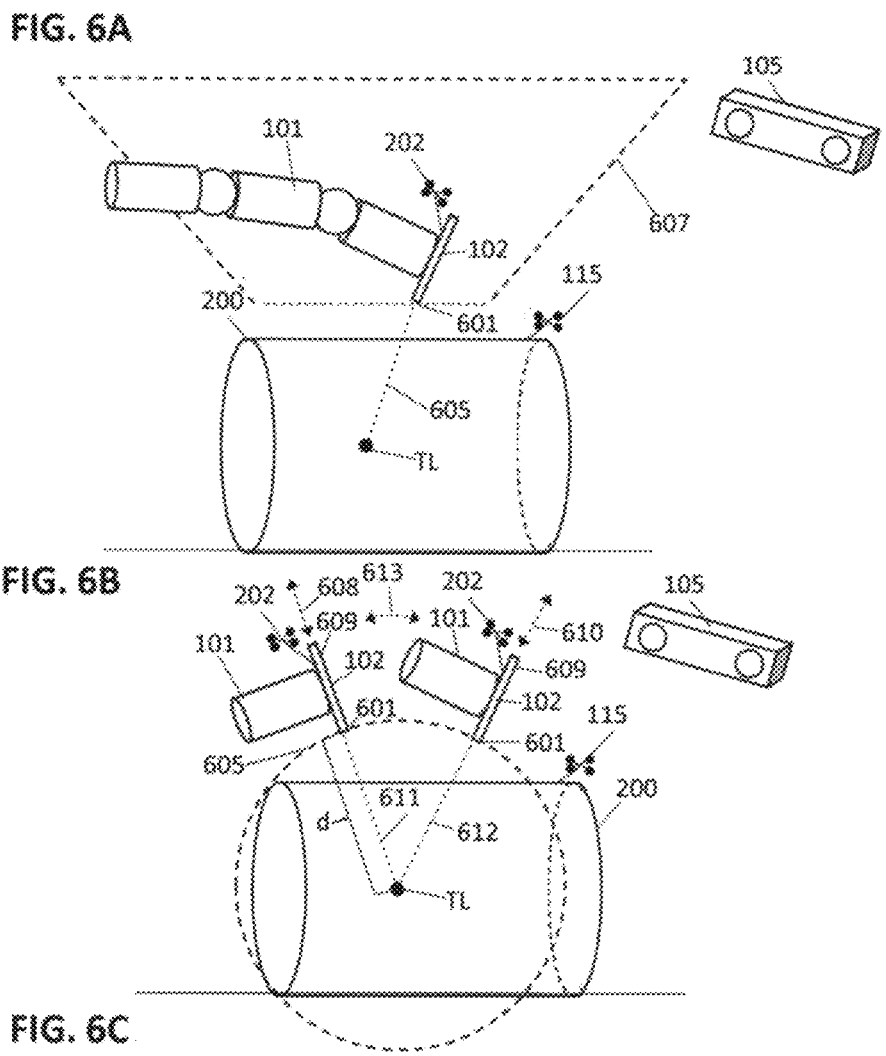
FIG. 6B
FIG. 6C

METHODS AND SYSTEMS FOR ROBOT-ASSISTED SURGERY

CROSS-REFERENCE TO RELATED APPLICATIONS

The subject patent application is a divisional of U.S. patent application Ser. No. 16/344,720, filed on Jun. 17, 2019, which is the National Stage of International Application No. PCT/US2017/058105, filed on Oct. 24, 2017, which claims priority to, and all the benefits of, United States Provisional Patent Application No. 62/412,422, filed on Oct. 25, 2016, the entire contents of which are incorporated by reference herein.

BACKGROUND

Computer-assisted surgical procedures, which may include image guided surgery and robotic surgery, have attracted increased interest in recent years. These procedures include the integration of a "virtual" three-dimensional dataset of the patient's anatomy, typically obtained using pre-operative or intra-operative medical imaging (e.g., x-ray computed tomography (CT) or magnetic resonance (MR) imaging), to the actual position of the patient and/or other objects (e.g., surgical instruments, robotic manipulator(s) or end effector(s) in the surgical area. These procedures may be used to aid the surgeon in planning a surgical procedure and may also provide the surgeon with relevant feedback during the course of surgical procedure. There is a continuing need to improve the safety and ease-of-use of computer-assisted surgical systems.

SUMMARY

Various embodiments include methods and systems for performing robot-assisted surgery.

Embodiments include a method for defining a boundary surface for a robotic surgery system that includes identifying at least a portion of a skin surface of a patent in an image dataset of the patient's anatomy, generating a boundary surface based on the identified skin surface, registering the image dataset and the boundary surface within a patient coordinate system, and controlling a robotic arm to prevent at least a portion of the robotic arm from crossing the boundary surface.

Further embodiments include a method for operating a robotic arm in an image-guided surgery system that includes defining a target location within the body of a patient in the image-guided surgery system, moving a robotic arm relative to the patient, and controlling the robotic arm to maintain an end effector of the robotic arm pointed along a trajectory that intersects with the target location while the robotic arm is moved relative to the patient.

Further embodiments include a robot assisted surgery system that includes a robotic arm, a motion tracking system configured to monitor a position of the robotic arm relative to a patient, and a secondary sensing device for detecting a movement of the patient relative to the robotic arm.

Further embodiments include a method for preventing a robotic arm from colliding with a patient that includes tracking at least one of a position and orientation of a robotic arm relative to a patient using a motion tracking system, detecting a movement of the patient relative to the robotic arm using a secondary sensing device, and controlling the robotic arm to take a remedial action based on a movement of the patient detected using the secondary sensing device.

Further embodiments include a method of operating a robotic arm in a surgical robotic system that includes defining a virtual three-dimensional volume over the surgical area of the patient within a patient coordinate system of an image guided surgery system, tracking a location of the robotic arm within the patient coordinate system, determining whether a portion of the robotic arm is located within the virtual three-dimensional volume, and modifying an operating mode of the robotic arm based on the determination of whether a portion of the robotic arm is located within the virtual three-dimensional volume.

Further embodiments include an end effector for a robotic arm that includes a cannula having an opening for inserting an invasive surgical tool through the cannula and into the body of a patient and a detector device that is configured to detect when a tool is located within the cannula.

Further embodiments include a method for performing robot assisted surgery that includes positioning an end effector of a robotic arm over a patient, wherein the end effector comprises a cannula having an opening for inserting an invasive surgical tool through the cannula and into the body of a patient, detecting whether a tool is located in the cannula, and controlling the robotic arm to prevent the arm from moving in a direction that is transverse to a trajectory defined by the cannula.

Further embodiments include a method for performing robot assisted surgery that includes identifying a surface of an anatomical feature within the body of a patient in an image dataset of the patient's anatomy, registering the image dataset within a patient coordinate system, generating a virtual three-dimensional surface corresponding to the surface of the anatomical feature of the patient outside of the body of the patient within the patient coordinate system, and controlling a robotic arm to provide haptic feedback to a user as a portion of the robotic arm is moved over the virtual three-dimensional surface.

Further embodiments include a robotic arm having a plurality of repeating segments coupled end-to-end, where each segment includes a first end portion, a second end portion, and a central portion having generally spheroid-shaped outer surface located between the first end portion and the second end portion, the first end portion and the second end portion having a smaller diameter than the central portion, and where each segment provides at least two rotational degrees of freedom such that an axis extending longitudinally through the second end portion may rotate in two mutually perpendicular directions with respect to an axis extending longitudinally through the first end portion.

BRIEF DESCRIPTION OF THE DRAWINGS

Other features and advantages of the present invention will be apparent from the following detailed description of the invention, taken in conjunction with the accompanying drawings of which:

FIG. 3 is a process flow diagram illustrating a method for performing registration of patient image data for image-guided surgery.

FIGS. 6A-6C schematically illustrate methods of controlling a robotic arm such that an end effector of the robotic arm maintains a trajectory that intersects with a pre-defined target location within the body of a patient.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1:
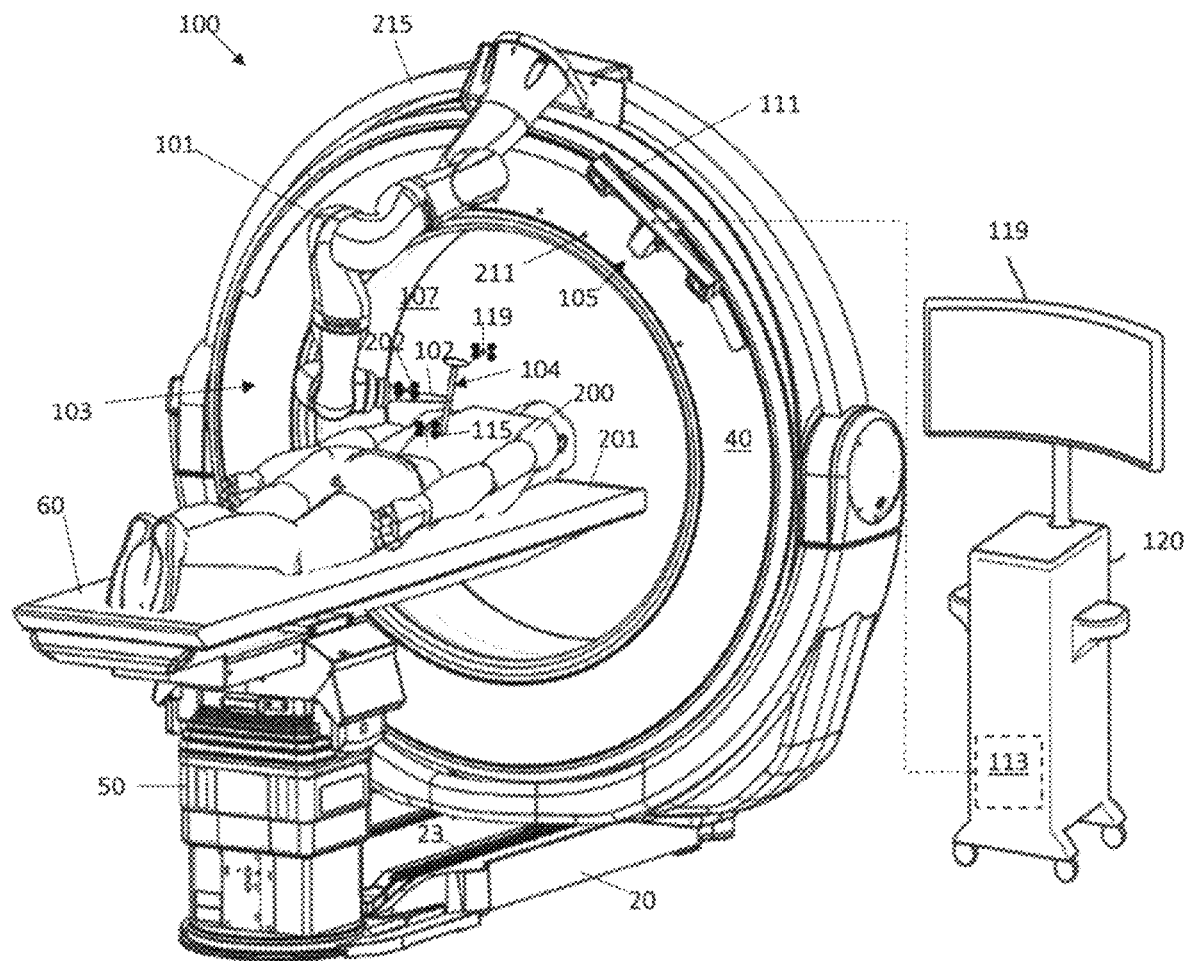
FIG. 1 is a perspective view of a system for performing robotically-assisted image-guided surgery according to an embodiment.

FIG. 1 illustrates a system 100 for performing robotically-assisted image-guided surgery according to various embodiments. The system 100 in this embodiment includes an imaging device 103, a motion tracking system 105 and a robotic arm 101 for performing a robotically-assisted surgical procedure. The robotic arm 101 may comprise a multi-joint arm that includes a plurality of linkages connected by joints having actuator(s) and optional encoder(s) to enable the linkages to rotate, bend and/or translate relative to one another in response to control signals from a robot control system. The robotic arm 101 may be fixed to a support structure at one end and may have an end effector 102 at the other end of the robotic arm 101.

The imaging device 103 may be used to obtain diagnostic images of a patient 200, which may be a human or animal patient. In embodiments, the imaging device 103 may be an x-ray computed tomography (CT) imaging device. The patient 200 may be positioned within a central bore 107 of the imaging device 103 and an x-ray source and detector may be rotated around the bore 107 to obtain x-ray image data (e.g., raw x-ray projection data) of the patient 200. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure) or intra-operatively (i.e., during a surgical procedure) by positioning the patient 200 within the bore 107 of the imaging device 103. In the system 100 of FIG. 1, this may be accomplished by moving the imaging device 103 over the patient 200 to perform a scan while the patient 200 may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient 200 may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient 200, and may translate away from the patient 200 to an out-of-the-way position for performing a surgical procedure on the patient 200.

An example imaging device 103 that may be used in various embodiments is the AIRO® intra-operative CT system manufactured by Mobius Imaging, LLC and distributed by Brainlab, AG. Other imaging devices may also be utilized. For example, the imaging device 103 may be a mobile CT device that is not attached to the patient support 60 and may be wheeled or otherwise moved over the patient 200 and the support 60 to perform a scan. Examples of mobile CT devices include the BodyTom® CT scanner from Samsung Electronics Co., Ltd. and the O-Arm® surgical imaging system form Medtronic, plc. The imaging device 103 may also be a C-arm x-ray fluoroscopy device. In other embodiments, the imaging device 103 may be a fixed-bore imaging device, and the patient 200 may be moved into the bore of the device, either on a surgical support 60 as shown in FIG. 1, or on a separate patient table that is configured to slide in and out of the bore. Further, although the imaging device 103 shown in FIG. 1 is located close to the patient 200 within the surgical theater, the imaging device 103 may be located remote from the surgical theater, such as in another room or building (e.g., in a hospital radiology department).

The motion tracking system 105 shown in FIG. 1 includes a plurality of marker devices 119, 202, 115 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and 115 and a stereoscopic optical sensor device 111 that includes two or more cameras (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and 115 and received by the cameras. The marker devices 119, 202, 115 may each include three or more (e.g., four) reflecting spheres, which the motion tracking system 105 may use to construct a coordinate system for each of the marker devices 119, 202 and 115. A computer 113 may be coupled to the sensor device 111 and may determine the transformations between each of the marker devices 119, 202, 115 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, a reference marker device 115 (e.g., reference arc) may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 119 may be attached to surgical tools 104 to enable the tools 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient 200.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Each moiré pattern marker may also include a unique identifier or code that may enable different objects within the camera's field of view to be uniquely identified and tracked. An example of an MPT-based tracking system is available from Metria Innovation Inc. of Milwaukee, Wis. Other tracking technologies, such as computer vision systems and/or magnetic-based tracking systems, may also be utilized.

The system 100 may also include a display device 119 as schematically illustrated in FIG. 1. The display device 119 may display image data of the patient's anatomy obtained by the imaging device 103. The display device 119 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 119, and may be shown overlaying the image data. In the embodiment of FIG. 1, the display 119 is located on a mobile cart 120. A computer 113 for controlling the operation of the display 119 may also be housed within the cart 120. In embodiments, the computer 113 may be coupled to the optical sensor device 111 and may also perform all or a portion of the processing (e.g., tracking calculations) for the motion tracking system 105. Alternatively, one or more separate computers may perform the motion tracking processing, and may send tracking data to computer 113 on the cart 120 via a wired or wireless communication link. The one or more separate computers for the motion tracking system 105 may be located on the imaging system 103, for example.

Figure 2:
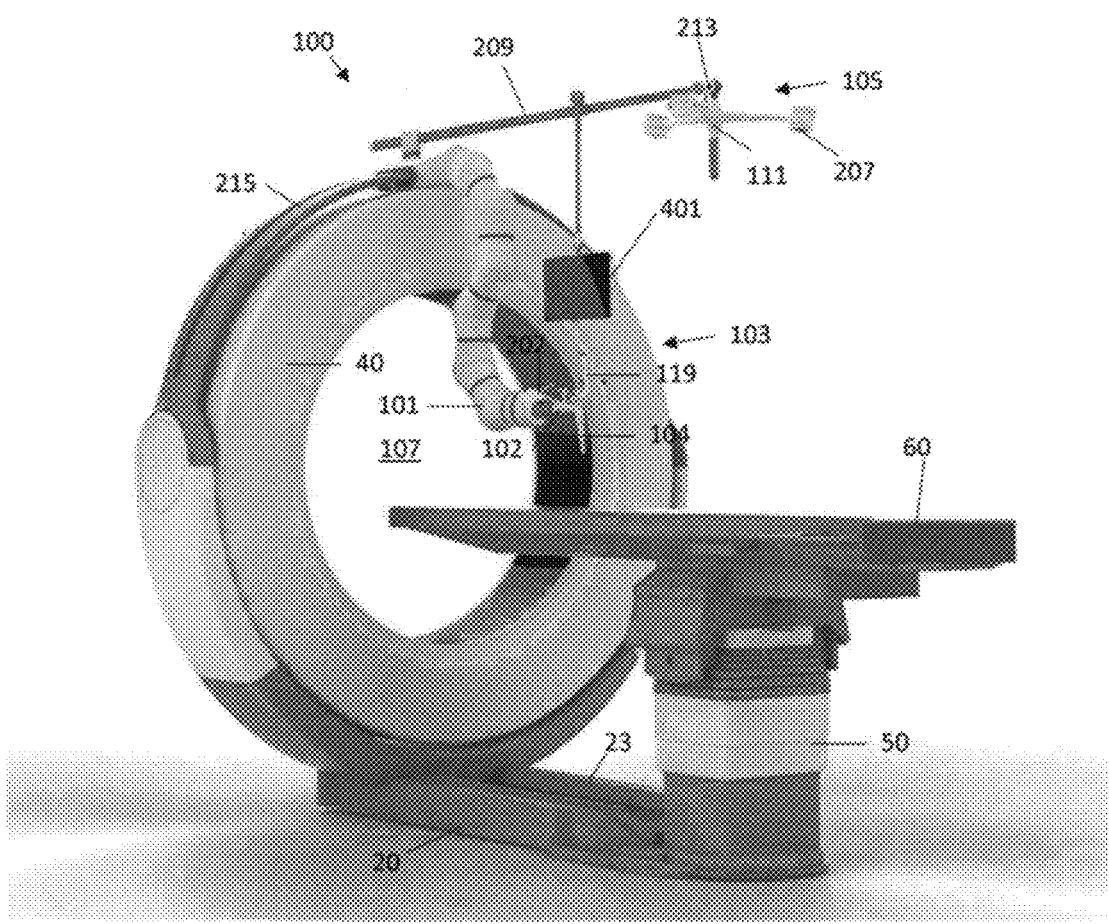
FIG. 2 shows an alternative embodiment of a system for performing robotically-assisted image-guided surgery having an optical sensing device for a motion tracking system on an arm extending from a gantry of an imaging system.

FIG. 2 illustrates an alternative embodiment in which the optical sensor device 111 includes a plurality of cameras 207 mounted to an arm 209 extending above the patient 200 surgical area. The arm 209 may be mounted to or above the imaging device 103. The arm 209 may also enable the sensor device 111 to pivot with respect to the arm 209 and/or the imaging device 103 (e.g., via one or more ball joints 213). The arm 209 may enable a user to adjust the position of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure. The positioning of the optical sensor device 111 on an arm 209 may also enable the cameras 207 to more easily view and track markers 211 (see FIG. 1) that may be located on the imaging device 103, such as on the outer surface of the gantry 40, which may be used during automatic registration of patient images, as described further below.

FIG. 2 also illustrates a display device that may comprise a handheld display device 401. As used herein, "handheld computing device" and "handheld display device" are used interchangeably to refer to any one or all of tablet computers, smartphones, pendant controllers, cellular telephones, personal digital assistants (PDA's), netbooks, e-readers, laptop computers, palm-top computers, wearable computers, and similar portable electronic devices which include a programmable processor and memory coupled to a display screen and may include hardware and/or software to enable display of information, including patient information and/or images, on the display screen. A handheld computing device typically also includes an antenna coupled to circuitry (e.g., a transceiver) to enable wireless communication over a network. A handheld computing or display device may be characterized by a sufficiently compact and lightweight structure to enable a user to easily grasp, maneuver and operate the device using one or both hands.

One or more handheld display devices 401 may be mounted to an arm 209 extending above the patient surgical area, as shown in FIG. 2. The arm 209 may also support the optical sensing device 111 for the motion tracking system 105, as described above. The one or more display devices 119 may be suspended from the arm 209, and the position of a display device 119 may be adjustable along the length of the arm 209. The display device 119 may be located within a sterile case or holder, such as described in U.S. application Ser. No. 15/701,063, filed on Sep. 11, 2017, which is incorporated by reference herein. In other embodiments, a handheld display device 119 may be mounted to the patient support 60 or column 50 or to any portion of the imaging system 103, or to any of the wall, ceiling or floor in the operating room, or to a separate cart. One or more handheld display devices 401 may be used in addition to or as an alternative to a conventional display device, such as a cart-mounted monitor display device 119 as shown in FIG. 1.

As shown in FIGS. 1 and 2, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. In further embodiments, the robotic arm 101 and/or the optical sensing device 111 may be mounted to a separate mobile shuttle, as described in U.S. application Ser. No. 15/706,210, filed on Sep. 15, 2017, which is incorporated by reference herein. Although a single robotic arm 101 is shown in FIGS. 1 and 2, it will be understood that two or more robotic arms 101 may be utilized.

FIG. 3 is a process flow diagram that illustrates a method 300 of registering patient images. Computer-assisted surgery techniques generally utilize a process of correlating a dataset representing a portion of the patient's anatomy that is to be operated on with the position of the patient at the time of the surgical intervention. The position of the patient may be determined based on a second image dataset which may include real-time camera image(s) from a motion tracking system 105 as described above. The correlation between these datasets may be accomplished computationally using software, and may be referred to as "patient registration." The registration method 300 of FIG. 3 may be implemented using one or more computing devices, such as computer 113 shown in FIG. 1.

In block 301 of method 300, a first image dataset of the patient's anatomy may be obtained using an imaging device, such as the imaging device 103 shown in FIGS. 1 and 2. The first image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The first image dataset may be stored electronically in a memory. The first image dataset may be in any suitable format, such as in a file format that conforms to the Digital Imaging and Communications in Medicine (DICOM) standard.

In block 303 of method 300, a second image dataset of the patient and the surrounding patient space may be obtained using a motion tracking system, such as the motion tracking system 105 shown in FIGS. 1 and 2. The second image dataset may indicate the current position and/or orientation of the patient. The second image dataset may include at least one image of a marker device that may be obtained using an optical sensing device 111 (e.g., cameras 207). The marker device (e.g., reference arc 115) detected by the optical sensing device 111 may be in a known fixed relationship with the surgically-relevant portion of the patient's anatomy. The motion tracking system 105 may determine the transformation between the marker device 115 and the optical sensing device 111 (e.g., using well-known triangulation techniques), and may thereby determine the transformation between the sensing device 111 (e.g., camera 207 position) and the surgically-relevant portion of the patient's anatomy. The motion tracking system 105 may similarly determine transformations between each of the other marker devices (e.g., marker devices 119 and 202 in FIG. 1) and the optical sensing device 111. Each of the markers 115, 119 and 202 being tracked may then be placed within a common coordinate system. In embodiments, the common coordinate system may have an origin or zero point that may be considered to be fixed relative to the surgically-relevant portion of the patient's anatomy, and may also be referred to the patient coordinate system.

In block 305 of method 300, the first image dataset may be registered to the common coordinate system as the second image dataset (e.g., the patient coordinate system). This may include performing a rigid transformation to map each pixel or voxel of the first image dataset into corresponding 3D coordinates (i.e., x, y, z coordinates) of the common coordinate system. A number of techniques may be utilized for registering multiple image datasets. In one non-limiting example of a registration process for x-ray CT imaging data, a pre-scan calibration process may be used to precisely calculate (e.g., within 1 mm and/or 1°) the transformation between the isocenter of the x-ray gantry 40 and the optical sensing device 111. A set of markers 211 (e.g., 3 or more, such as 4-6 markers) may be provided on the surface of the gantry 40, as shown in FIG. 1. The markers 211 may be within the field of view of the optical sensing device 111 to enable the gantry 40 position to be tracked by the motion tracking system 105. A calibration phantom (not shown for clarity) having a marker device (e.g., similar to marker device 115 in FIG. 1) fixed thereto may be placed on the patient support 60 such that the marker device is also within the field of view of the optical sensing device 111. The motion tracking system 105 may determine the transformation between the gantry 40 coordinate system defined by the markers 211 and the optical sensing device 111 coordinate system as well as the transformation between the phantom coordinate system defined by the marker device on the phantom and the optical sensing device 111 coordinate system. These transformations may be used to determine the gantry-to-phantom transformation. The phantom may then be scanned using the imaging device 103. A set of elements (e.g., x-ray visible beads) that may be easily identified from the imaging data may be located in the phantom, where the geometry of these elements within the phantom coordinate system may be previously-known. An algorithm may be used to analyze the x-ray image data to identify the x-ray visible elements with respect to the center point of the image data, which corresponds to the isocenter of the gantry 40. Thus, the x-ray visible elements may be located in a coordinate system having an origin at the isocenter of the x-ray gantry 40, and the transformations between the isocenter and the phantom and the isocenter and the markers 211 on the gantry 40 may be calculated.

During a subsequent scan of the patient 200, the position and orientation of the patient 200 with respect to the isocenter of the imaging device 103 may be determined (i.e., by tracking the positions of the markers 211 on the gantry 40, which are known with respect to the isocenter, and the patient reference arc 115, which is known with respect to the surgically-relevant portion of the patient anatomy). This may enable the image data obtained during the scan to be registered into the patient coordinate system.

In an alternative embodiment, the position of the optical sensing device 111 may be known relative to the imaging system 103 with sufficient accuracy such that the image dataset of the patient's anatomy obtained using the imaging system 103 may be registered in the common coordinate system of the patient without the motion tracking system 105 needing to track the position or orientation of the imaging system 103. In embodiments, separate markers 211 on the gantry 40 of the imaging system 103 as shown in FIG. 2 may not be required or used. In some embodiments, the position of the optical sensing device 111 (e.g., the position of each of the cameras 207 as shown in FIGS. 1 and 2) may be known relative to the isocenter of the gantry 40 of the imaging system 103, such as via a calibration process that may be performed at the factory or during installation or pre-calibration of the system. The gantry 40 and/or the optical sensing device 111 may include keying features (e.g., high-precision bolt patterns) where the optical sensing device 111 attaches to the gantry 40 to ensure that the position of the sensing device 111 on the gantry 40 remains accurately fixed. In embodiments where the camera(s) 207 may be movable relative to the gantry 40, high-precision encoders may precisely record and correct for any changes in camera position/orientation relative to the isocenter of the gantry 40. During imaging scans, the optical sensing device 111 may track the position and orientation of the patient 200 with respect to the camera position, which is in a known, fixed geometric relationship with the isocenter of the imaging device 103. The image data obtained during a scan may thus be registered into the common coordinate system of the patient without needing to first perform a calibration scan on a phantom, as described above.

In block 307 of method 300, images of the patient's anatomy from the first image dataset may be displayed with an overlay of one or more features derived from the second image dataset in the common coordinate system. The images may be displayed on a suitable display device, such as display 119 shown in FIG. 1. The images of the patient's anatomy may include 2D slices of a three-dimensional image dataset (e.g., a tomographic reconstruction) and/or a 3D volume rendering of all or a portion of the image dataset. In embodiments, images obtained using multiple imaging devices or imaging modalities may be fused and displayed in a common coordinate system. For example, the first image dataset of the patient's internal anatomy may be an x-ray CT scan. Another image dataset of the patient's internal anatomy, such as an MRI scan, may be combined with the x-ray CT data and displayed on the display 119. The MRI scan data may be registered into the common coordinate system using a similar registration process as described above. Alternately or in addition, an algorithm for matching landmarks or fiducials identifiable from both image datasets may be used to merge the datasets for display.

The one or more features derived from the second image dataset that may be displayed overlaying the images of the patient's anatomy may include graphical depictions of a tool 104, an end effector 102 or another object that is tracked by the motion tracking system 105. The graphical depiction may be based on a known geometry of the tool 104, end effector 102 or another object. The graphical depiction may be a rendering of the actual size and shape of the object or may be a depiction of select features of the object, such as a location of a tip end of the object and/or an orientation of the object. The graphical depiction may also indicate a trajectory defined by the object (e.g., a ray extending from a tip end of the object into the patient) and/or a target point within the patient's anatomy that may be defined based on the position and/or orientation of one or more objects being tracked. In various embodiments, the tool 104 may be a pointer. The tool 104 may also be a surgical instrument, such as a needle, a cannula, a dilator, a tool for gripping or cutting, an electrode, an implant, a drill bit, a screw, a screw driver, a radiation source, a drug and an endoscope. In embodiments, the end effector 102 of the robotic arm 101 may include a hollow tube or cannula that may be configured to hold one or more tools, such as a surgical instrument, and may be used to guide an instrument as it is inserted into the patient's body. Alternately, the end effector 102 itself may be or may include an instrument that may be inserted into the patient's body.

The motion tracking system 105 may repeatedly acquire new images from the optical sensing device 111, and the relative positions and/or orientations of objects within the field of view of the optical sensing device 111 may be updated with each acquisition of new images from the optical sensing device 111. The display 119 may be updated to reflect any change(s) in the position and/or orientation of the objects within the common coordinate system (e.g., relative to the patient reference arc 115), which may include adding additional graphical elements to depict new objects that are moved within the field of view of the optical sensing device 111 and removing graphical depictions of objects when they are no longer within the field of view of the optical sensing device 111. In some embodiments, the optical sensing device 111 may include a motorized system to enable the position and/or orientation of the camera(s) 207 to move to maintain the surgical area within the center of the field of view of the camera(s) 207.

Figure 4:
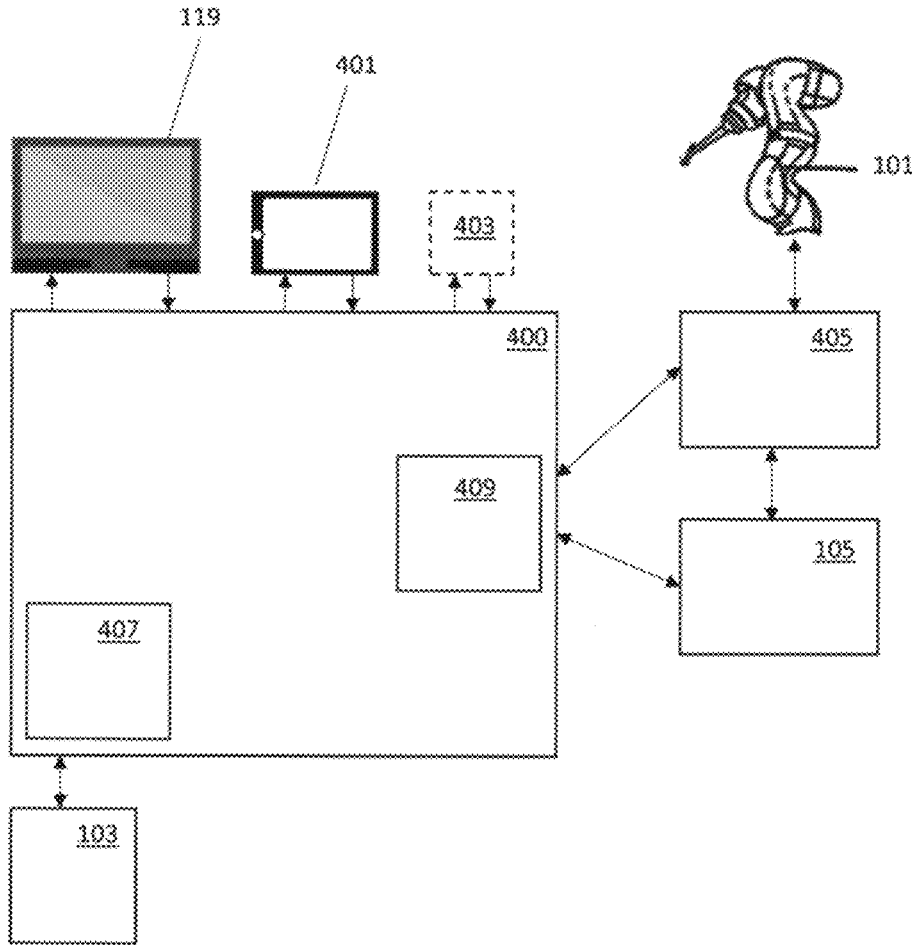
FIG. 4 is a block diagram schematically illustrating a system for robotically-assisted image-guided surgery according to an embodiment.

FIG. 4 is a component block diagram of an image-guided surgery system 400 according to an embodiment. The system 400 may be implemented using one or more computing devices, such as computer 113 shown in FIG. 1. The system 400 may be operatively coupled to a first display device 119, which may include a monitor that is fixed to a cart 120 or other structure (e.g., wall, ceiling, floor, imaging device, etc.) within the operating suite. The system 400 may also be operatively coupled to at least one additional display device 401, which may be a handheld computing device, as described above. The system 400 may also include an audio input/output component 403, which may include a speaker or other output component for outputting audible signals (e.g., audio instructions, alerts, etc.) and/or a microphone or other input component for receiving audio inputs (e.g., voice commands) that may be interpreted by the system 400. The system 400 may be implemented at least partially in software and may be based on one or more of the Image-Guided Surgery Toolkit (IGSTK), Visualization Toolkit (VTK) and Insight Segmentation and Registration Toolkit (ITK) development frameworks.

The system 400 may be configured to receive and store imaging data 407 (e.g., DICOM data) collected by an imaging device 103. The imaging data 407 may be received directly from the imaging device 103 or may be retrieved from another source, such as a remote server. The imaging data 407 may be imaging data that is obtained prior to a surgical procedure (e.g., pre-operative image data) and/or imaging data that is obtained during a surgical procedure (e.g., intra-operative image data). In embodiments, the system 400 may be configured to display the most-current image data 407 collected by the imaging device 103. The image data 407 may be registered to a common coordinate system as the tracking data 409 from the motion tracking system 105 in accordance with a registration method such as method 300 described above with reference to FIG. 3.

The system 400 may also receive tracking data 409 from a motion tracking system 105. The system 400 may be configured to repeatedly read the tracking data from the motion tracking system 105 indicating the current position/orientation of the patient and any other objects tracked by the motion tracking system 105. The system 400 may read the tracking data at a frequency (e.g., refresh rate) of greater than 100 Hz (e.g., 240 Hz). In embodiments, the tracking data from the motion tracking system 105 may include data to enable the system 400 to identify particular objects from within the tracking data. For example, each marker device (e.g., marker devices 115, 202 and 119 in FIG. 1) may include a unique characteristic (e.g., a unique geometric pattern of reflective markers, a unique flash pattern of active markers, etc.) to enable the marker device to be identified. These unique characteristics of the marker devices may be registered with particular objects or tools (e.g., associated with a particular object or tool in a database) by the system 400. The unique characteristics of the marker devices may be pre-registered in the system 400 and/or may be registered to particular objects or tools during the course of a surgical procedure. The system 400 may also include a library of graphical elements that may be associated with particular objects or tools (e.g., in a database). The system 400 may display graphical elements associated with the objects or tools being tracked by the motion tracking system 105 in the common coordinate system with the image data on the display(s) 119, 401.

The system 400 may include a user-interface component that may control the display of system information and/or graphical user interface elements on the display(s) 119 and 401. The system 400 may further process and implement user commands received from user interface devices. A user interface device, may include, for example, a touchscreen user interface which may be integrated with a display device 119, 401. In embodiments, a user interface device may alternately or additionally include one or more of a button, a keyboard, a joystick, a mouse, a touchpad, etc. which may be located on a display device 119, 401 and/or on a workstation (e.g., a workstation located on a cart 120). In embodiments, the user interface device(s) may also include a microphone (e.g., audio input/output component 403) that may receive voice commands that may be interpreted by the system (e.g., using voice recognition software). The user commands received via one or more user input devices may enable a user to control various functions of the system 400, such as changing what is shown on the display(s) 119, 401 (e.g., displaying different image datasets, displaying different slice(s) and/or different 3D rendering(s) within an image dataset, zooming in or out of an image, displaying different menu options, returning to a home screen, etc.). In embodiments, the user commands may enable a user to set one or more trajectories and/or target locations within the patient's anatomy. The system 400 may store the positions and/or orientations of user-defined trajectories or target locations within the common coordinate system, and may display graphical representations of such trajectories or target locations on the display(s) 119, 401.

The user commands received by the system 400 may also include commands for controlling the operation of other components, such as the imaging device 103, the motion tracking system 105 and/or a robotic arm 101. For example, for a robotically-assisted surgical procedure, the user command may include an instruction to move a robotic arm 101 to a particular position and/or orientation. The instruction to move the robotic arm 101 may be based on a user interaction with image data of the patient's anatomy that is displayed on a display device 119, 401. For example, the user may use the display device 119, 401 to define a particular trajectory with respect to the patient's anatomy and may send an instruction for the robotic arm 101 to move such that that the end effector 102 of the robotic arm 101 is positioned along the defined trajectory.

A robotic control system 405 may control the movement of one or more robotic arms 101. The robotic control system 405 may receive sensor data indicating the current parameters of the robotic arm 101 (e.g., robot position, joint angles, measured axis forces, motor currents) and may send motor control signals to drive the movement of the arm 101. In embodiments, the motion tracking system 105 may track the position of the robotic arm 101 (e.g., via marker device 202 on end effector 102 as shown in FIG. 1) to determine the position of the end effector 102 within the common coordinate system of the patient. A control loop, which may be executed using the image-guided surgery system 400, the motion tracking system 105 and/or the robotic control system 405, may continuously read the tracking data and the robot parameter data and may send instructions to the robotic control system 405 to cause the robotic arm 101 to move to a desired position and orientation.

In various embodiments, display device 119 may be a primary display device (e.g., a monitor) that may be connected to the image-guided surgery system 400 by a wired or wireless link. In one embodiment, the system 400 may stream video data to the display device 119 over a suitable video data interface (e.g., an HDMI interface) and may also exchange other signals with the display device over a separate data connection (e.g., a USB connection).

In various embodiments, display device 401 may be a handheld computing device. A handheld display device 401 may generally be smaller and lighter than the primary display device 119 (e.g., monitor), and may in certain embodiments be referred to as a secondary display device. In some embodiments, display device 401 may be a mirror of display device 119 and may display all or a portion of the same information as is shown on display device 119. Alternately, display device 401 may display different information than is shown on display device 119. In some embodiments, display device 119 may be omitted, and handheld display device 401 may be the only display device operably connected to the image-guided surgery system 400. In such a case, display device 401 may be referred to as the primary display device. Further, although a single handheld display device 401 (i.e., a tablet computer) is shown in FIG. 4, it will be understood that multiple handheld display devices 401 may be simultaneously connected to and used with the system 400.

The handheld display device 401 may be coupled to the image-guided surgery system 400 by a wired or wireless communication link. In one embodiment, the handheld display device 401 may communicate with the system 400 over a wireless communication interface. The system 400 may stream digital video data (e.g., high-definition video) for display on the handheld display device 401, such as over a wireless local area network (WLAN) connection, including a IEEE 801.11 (e.g., WiFi) connection. The system 400 may also exchange other signals with the handheld display device 401 (e.g., control signals from the system 400 and/or user commands received at a user interface, such as a touchscreen, on the display device 401) over a wireless connection. The system 400 and the display device 401 may communicate over any suitable wireless protocol or standard, such as over a IEEE 802.15x (e.g., a BLUETOOTH®) connection.

An image-guided surgical system 400 according to various embodiments may provide a plurality of modes for displaying patient information. For example, a first display mode may include displaying a 3D image dataset (e.g., an x-ray CT, MRI, sonogram, PET or SPECT image dataset) in multiple two-dimensional slices corresponding to anatomic planes (e.g., axial, sagittal, coronal planes) transecting the patient. This is illustrated in the screenshot of a display device shown in FIG. 5. The display device may be a display device 119 (e.g., monitor) as shown in FIG. 1 or a handheld display device as shown in FIGS. 2 and 4. The display screen 500 in this example illustrates four different patient images in four quadrants of the display screen 500. Three of the quadrants (i.e., top left, top right and bottom left quadrants of display screen 500) depict different two-dimensional slices 501, 503, 505 of CT image data. A fourth quadrant (i.e., lower left quadrant of display screen 500) includes a 3D volume rendering 507 illustrating a "virtual" view of anatomic feature(s) (e.g., bony structures or other discrete internal anatomic features). The two-dimensional slices 501, 503, 505 correspond, respectively, to views taken along axial, sagittal and coronal planes through the patient 200.

Figure 5:
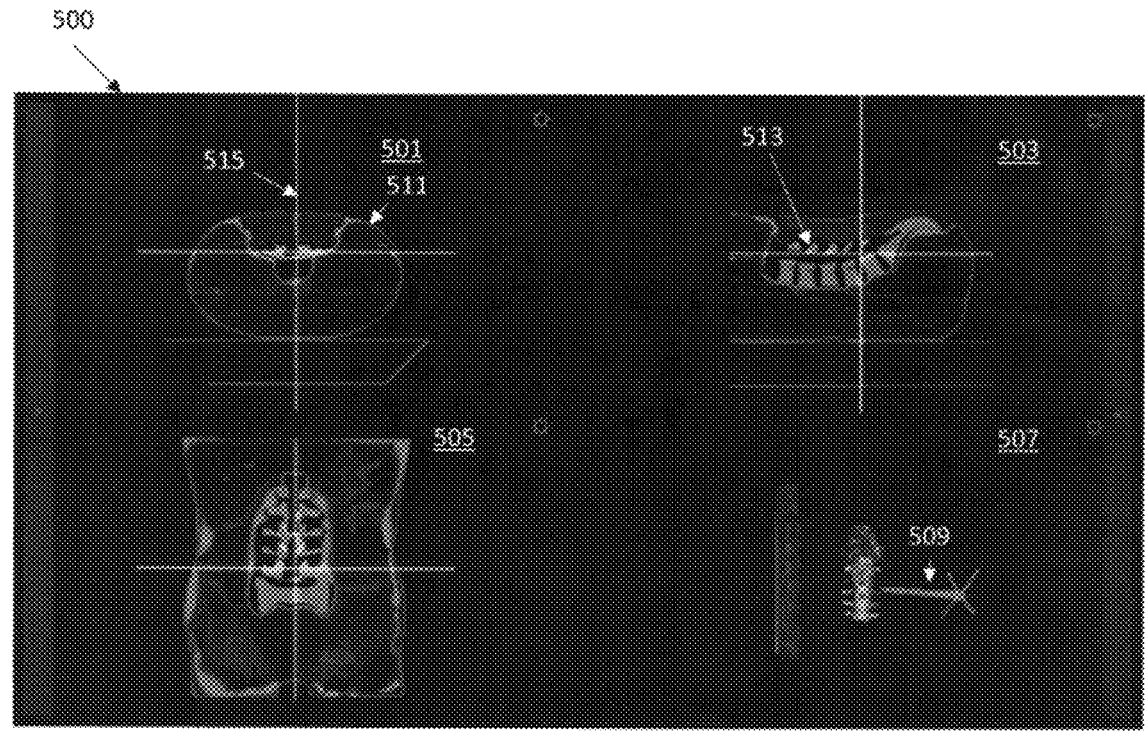
FIG. 5 illustrates a display screen of a display device in an image-guided surgery system according to an embodiment.

The display screen 500 may also display graphical elements illustrating the relationship of each slice 501, 503, 505 relative to the other slices shown on the display screen 500. For example, as shown in FIG. 5, the axial slice 501 image data may include an overlay of a cross pattern 515 showing the intersection of the axial slice 501 with the planes corresponding to the sagittal and coronal slices 503 and 505 shown on the display screen 500. Similar cross patterns 515 may be displayed overlaying the display of image data in the sagittal and coronal slices 503 and 505. The display screen 500 may also include graphical representations or renderings of other objects or tools tracked by the motion tracking system 105. In the example of FIG. 5, a graphical representation of a tool 509 is shown in the lower right quadrant of the display screen 500. The graphical representation of the tool 509 may illustrate the position and orientation of the tool relative to the anatomic features depicted in the 3D volume rendering 507. Similar graphical elements may be displayed in the 2D slice images 501, 503 and 505 to illustrate the position and/or orientation of one or more objects with respect to the patient.

It will be understood that the four-quadrant view shown in FIG. 5 is one possible implementation of a display of patient information on a display device 119, 401. Other possible display modes are possible. For example, rather than illustrating multiple different images (e.g., slices) from a patient image dataset (e.g., reconstructed volume), the display screen 500 may show only a single image (e.g., a single axial, sagittal or coronal slice 501, 503, 505 or a single 3D volume rendering 507). The display screen 500 may illustrate only two slices corresponding to different anatomic planes (e.g., axial and sagittal, axial and coronal, or sagittal and coronal slices), or may illustrate a single slice along with a 3D volume rendering. In some embodiments, the display screen 500 may illustrate multiple two-dimensional slices corresponding to the same anatomic planes (e.g., multiple axial, sagittal and/or coronal slices taken through different sections of the reconstructed volume) and/or multiple 3D volume renderings viewed from different angles. The different images and display modes of the display screen 500 may be customizable based on user selections, which may be made via a user input device and/or user voice commands. In embodiments, the user may be able to select (e.g., scroll through) different patient images, such as sequentially illustrating multiple axial, sagittal and/or coronal slices taken through different sections of the reconstructed volume, or sequentially illustrating multiple 3D volume renderings viewed from different angles. The display screen 500 may also display slices along oblique planes taken through the reconstructed volume. The user may also have the capability to control the magnification of images, such as by zooming into or out from a particular portion of an image shown in the display screen 500. The user may control the selection of patient images for display using a user input device, voice commands and/or via a separate tool, such as a pointer device. In some embodiments, the intersection of the three image planes (i.e., axial, sagittal and coronal) shown on the display panel 500 may coincide with a target position within the patient's body. The surgeon may use the display panel 500 as a "virtual cutting tool" to move through the various slices/views of the patient image volume and to identify and select a target region for a surgical intervention.

The user (e.g., a surgeon) may be able to set one or more target positions and/or trajectories within the patient 200. There may be a variety of ways to set a trajectory or target location. For example, the surgeon may move through different views of the patient image data by manipulating a tool (e.g., a pointer/stylus device and/or an end effector of a robotic arm) over the patient 200, where the tool may define a unique trajectory into the patient. The tool may be tracked within the patient coordinate system using the motion tracking system 105. In some embodiments, an imaginary ray projected forward from the tip end of the tool may define the unique trajectory into the patient, which may be graphically depicted on the display screen 500. A target location along the unique trajectory may be defined based on a predetermined offset distance from the tip end of the tool. Alternately, the surgeon may directly manipulate and interact with the displayed image data to identify a particular target or trajectory, such as using a workstation computer. A particular target point or trajectory may be set by the system 400 in response to an input event, which may include, for example, a voice command, a touch event on a touchscreen interface, and/or an input on a user interface device (e.g., a keyboard entry, a mouse click, a button push, etc.). In embodiments, the surgeon may set a target position and/or trajectory by interacting with image data displayed on a display device, such as display devices 119 and/or 401. For example, the surgeon may define a target point and/or trajectory in the patient 200 by selecting one or more points on a display screen 500 of a display device 119, 401 (e.g., marking the points using a stylus, a cursor or mouse pointer, or a touch on a touchscreen user interface). To define a trajectory, for instance, the user may select two or more points in the image data (e.g., a target point and an entrance point on the skin of the patient). In embodiments, the user may be able to make fine adjustments to a selected target point and/or trajectory using any suitable user interface device. Multiple target points and/or trajectories may be set and saved in a memory (e.g., in an image-guided surgery system 400 as illustrated in FIG. 4), where each target point and/or trajectory may be saved in association with a unique identifier (e.g., file name).

In embodiments, the display screen 500 may display graphical element(s) overlaying the image data corresponding to one or more target locations and/or trajectories that are set by the user. For example, defined target locations may be illustrated as identifiable dots or points in the image data, which may be color coded and/or labeled on the display screen 500 to enable easy visualization. Alternately or in addition, defined trajectories may be depicted as identifiable lines or line segments in the image data, which may be similarly color coded and/or labeled. As discussed above, the display screen 500 may also display graphical elements associated with particular tools or objects, including invasive surgical tools or instruments, that are tracked by the motion tracking system 105. In embodiments, the display screen 500 may depict at least a portion (e.g., a tip end) of a surgical instrument as it is inserted into the patient 200, which may enable the surgeon to track the progress of the instrument as it progresses along a defined trajectory and/or towards a defined target location in the patient 200.

The at least one robotic arm 101 may aid in the performance of a surgical procedure, such as a minimally-invasive spinal surgical procedure or various other types of orthopedic, neurological, cardiothoracic and general surgical procedures. In various embodiments, a robotic arm 101 may be operated in a number of different operating modes. For example, the robotic arm 101 may operate in a hand guiding mode in which the movement of the robotic arm 101 may be controlled based on a force applied by a user to the arm (e.g., using torque and/or force sensing feedback to a robotic control system 405 as shown in FIG. 4). The robotic arm 101 may also operate in an autonomous mode in which the robotic arm 101 moves to particular poses in response to control signals from the robotic control system 405 (e.g., in accordance with a robotic motion planning algorithm and/or in response to signals from a separate user controller device, such as a joystick controller). The robotic arm 101 may also operate in a static or braked mode in which the robotic arm 101 may hold a particular pose and does not move. In some embodiments, the robotic arm 101 may also operate in various additional modes that may be combinations of the modes described above. For example, the robotic arm 101 may operate in a hybrid mode in which the robotic arm 101 (or a portion thereof) may be moved by hand guiding for certain movements of the arm (e.g., along certain directions or orientations) but may be rigid (e.g., braked) and/or provide increased resistance to other movements of the arm.

In some embodiments, the surgeon may move the robotic arm 101 in hand guiding mode over the patient 200 to cause the display screen 500 to display various views or slices of the patient image volume, which may be based on the tracked position of the end effector 102 of the robotic arm 101 within the patient coordinate system. Based on the image data displayed on the display screen 500, the user may set a particular target position and/or trajectory using a voice command or another input event as described above. In some embodiments, in response to the user setting a target position or trajectory, the robotic arm 101 may be configured to hold its current pose with the tip end of the end effector 102 pointing along the pre-determined trajectory to the target position within the patient's body. Alternately, the target position and/or trajectory may be defined using another method (e.g., using a pointer device or via user interaction with a display device 119, 401) and/or the target position/trajectory may be previously set and stored in a memory. In response to a user command for the robotic arm 101 to go to the target position or trajectory, the robotic arm 101 may be configured to autonomously move to a pose with the tip end of the end effector pointing along the pre-determined trajectory to the target position.

In some embodiments, when the robotic arm 101 is pointed along a set trajectory to a target position, the robotic arm 101 may maintain a rigid or fixed pose to enable the surgeon to insert an instrument or tool through a cannula arranged along a vector that coincides with the predefined trajectory into the body of the patient 200. The cannula may be a portion of the end effector 102 of the robotic arm 101 or it may be separate component that is held by the end effector 102. The cannula may be positioned by the robotic arm 101 such that the central axis of the cannula is collinear with the pre-defined trajectory into the patient 200. Alternately or in addition, the robotic arm 101 may operate in a hybrid or compliant mode such that the robotic arm 101 may be hand guided in a limited range of motion (e.g., along the set trajectory towards or away from the patient 200) while all other motions may be braked. In some embodiments, the robotic arm 101 may be hand guided with increased resistance and/or reduced velocity around the initial set trajectory to enable the surgeon to make fine adjustments to the position and/or orientation of the trajectory. In other embodiments, the robotic arm 101 may enable a degree of compliance or movement with respect the set trajectory in response to an applied force on the arm, but may be configured to "snap back" to the initial set trajectory when the applied force is released.

FIGS. 6A and 6B schematically illustrate an operating mode of a robotic arm 101 in which the robotic arm 101 is moved so as to maintain the tip end 601 of the end effector 102 pointed along a trajectory that intersects with a defined target location, TL, within the body of a patient 200. The target location, TL, may be defined and stored within the patient coordinate system in any manner as described above. As shown in FIG. 6A, the robotic arm 101 may be in a first pose with the tip end 601 of the end effector 102 pointed along a first trajectory 603 that intersects with the target location, TL. The robotic arm 101 may be moved to a second pose relative to the patient 200 (e.g., laterally and/or axially over the skin surface of the patient 200) while maintaining the tip end 601 of the end effector 102 pointed along a trajectory that intersects with the target location, TL. As shown in FIG. 6B, the end effector 102 is pointed along a second trajectory 605 that intersects with the target location, TL. The movement of the robotic arm 101 may be a hand guided movement (e.g., in response to a force applied the user) or an autonomous movement (e.g., based on a robotic motion planning algorithm). In either case, the robotic control system 405 may control the motion of the robotic arm 101 such that the tip end 601 of the end effector 102 is maintained pointed along a trajectory that intersects with the target location, TL. In embodiments, this may include executing a control loop that repeatedly reads the joint parameters of the robotic arm 101 while monitoring the tracking data indicating the current position and orientation of the end effector 102 with respect to the target location in the patient coordinate system and sends control signals to the robotic arm 101 to control the motion of the arm 101 to maintain the tip end 601 of the end effector 102 pointed towards the target location, TL.

In one exemplary embodiment, a surgeon may set a target location, TL, within the patient without specifying a particular trajectory for reaching the target location. The robotic arm 101 may enable hand guiding over at least a limited range of motion such that the tip end of the end effector 102 is always pointed along a trajectory that intersects with the set target location, TL, in the patient's body. This may enable the surgeon to move the end effecter 102 over the surface of the patient 200 to find a preferred entry point and/or pathway into the patient to reach the target location. The robotic arm 101 may enable hand guiding of at least a portion of the robotic arm over at least a limited range of motion while the robotic control system 405 may control the robotic arm 101 to make compensating movements (e.g., based on the inverse kinematics of the robotic arm 101) to maintain the tip end 601 of the end effector 102 pointed at the target location, TL. For example, this may enable the surgeon to move a portion of the robotic arm 101 out of his or her way while maintaining the end effector 102 pointed at the target location, TL.

In some embodiments, the robotic arm 101 may be operated so as to compensate for any movement of the patient 200. For example, in response to a movement of the patient 200 with respect to the robotic arm 101, which may be detected via the motion tracking system 105, the robotic arm 101 may automatically make compensating movements to maintain the tip end 601 of end effector 102 pointed along trajectory that intersects with the target location, TL.

In some embodiments, the range of motion of the robotic arm 101 may be restricted such that the end effector 102 of the robotic arm 101 may only be moved (via hand guiding, autonomous motion, or both) within an imaginary cone or conical frustum having an apex that coincides with the target location, TL. Within the imaginary cone/frustum, the end effector 102 may be moved so as to maintain the tip end 601 of the end effector 102 pointed along a trajectory that intersects with the target location, TL. FIG. 6B schematically illustrates a conical frustum (depicted in cross-section by dotted line 607) within which the motion of the end effector 102 is restricted. The geometry of the cone or conical frustum 607 within which the end effector 102 is restricted (e.g., the slant height, radius of the top and/or base of the cone/frustum) may be adjustable by the user.

In a further embodiment operating mode of a robotic arm 101, the motion of the robotic arm 101 may be restricted such that the tip end 601 of the end effector 102 may not be moved within a pre-determined off-set distance from a defined target location, TL, inside the body of a patient 200. Put another way, the off-set distance may function as a stop on the motion of the end effector 102 towards the target location, TL. The stop may be located outside the body of the patient such that the end effector may be prevented from contacting the patient. In some embodiments, the robotic arm 101 may be movable (e.g., via hand guiding, autonomously, or both) in a limited range of motion such that the end effector 102 may only be moved along a particular trajectory towards or away from the patient 200 and may not be moved closer than the off-set distance from the target location, TL. This is illustrated by FIG. 6C, which schematically illustrates an offset distance, d, from the target location, TL. In this embodiment, the end effector 102 may be constrained to move in a direction towards or away from the patient 200 (indicated by arrow 608) coinciding with trajectory 611, but may not be moved closer than the offset distance, d. The offset distance may be a default parameter and/or may be adjustable by the user.

In some cases, the offset distance, d, may be selected based on the known geometry of an invasive surgical instrument that may be inserted through a cannula 609 that is formed by or attached to the end effector 102. The instrument may be, for example, a needle, a cannula, a dilator, a tool for gripping or cutting, an electrode, an implant, a drill bit, a screw, a screw driver, a radiation source, a drug and an endoscope. The instrument and/or the cannula 609 may include one or more features that operate as a mechanical stop as the instrument is advanced through the cannula such that the instrument may not be advanced beyond the mechanical stop. For example, the instrument may have a flange or similar feature near its distal end that contacts against the distal end of the cannula 609 (i.e., opposite the tip end of the cannula 609) to prevent further advancement of the instrument within the cannula 609. The offset distance, d, may be selected to prevent the tip end of the instrument from being advanced within the cannula 609 beyond the target location, TL, within the patient's body. In particular, the offset distance, d, may be selected based on a length of the instrument such that when the instrument is fully advanced within the cannula 609, the end effector 102 including the cannula 609 and instrument may not be advanced beyond a point outside of the patient 200 that would allow the tip end of the instrument to be advanced further than the target location TL within the patient 200.

In further embodiments, the robotic arm 101 may be movable (e.g., via hand guiding, autonomously, or both) in a limited range of motion such that the end effector 102 may maintain the tip end 601 of the end effector 102 pointed along a trajectory that intersects with a defined target location, TL, within the body of a patient 200 and may not be moved closer than a pre-determined off-set distance, d, from the target location, TL. This is illustrated in FIG. 6C, which shows the motion of the end effector 102 in the direction of arrow 613. Similar to the embodiment of FIGS. 6A-6B, the robotic control system 405 may control the motion of the robotic arm 101 such that the tip end 601 of the end effector 102 is maintained pointed along a trajectory 611, 612 that intersects with the target location, TL. Additionally, the robotic control system 405 may control the motion of the robotic arm 101 such that the tip end 601 may not be moved closer than the offset distance, d, to the target location, TL. Put another way, the tip end 601 of the end effector 102 may be constrained to move over a "virtual" spherical surface centered on the target location, TL, and having a radius equal to the offset distance, d. FIG. 6C schematically illustrates a virtual spherical surface (depicted in cross-section by dotted line 615) over which the motion of the tip end 601 of the end effector 102 is constricted. In some embodiments, the end effector 102 may be movable towards and away from the surface 615 (in the direction of arrows 609 and 610) while maintaining the cannula 609 aligned with respective trajectories 611, 612. In other embodiments, the motion of the robotic arm 101 may be controlled such that the tip end 601 of the end effector 102 is constrained to enable movement only over the virtual spherical surface 615. In some embodiments, the virtual surface 615 may comprise a full spherical surface which surrounds the target location, TL, in all dimensions. Alternately, the surface 615 may correspond to only a portion of a spherical surface, such as a spherical dome or cap that may encompass all or a portion of the surgical area.

Figure 7:
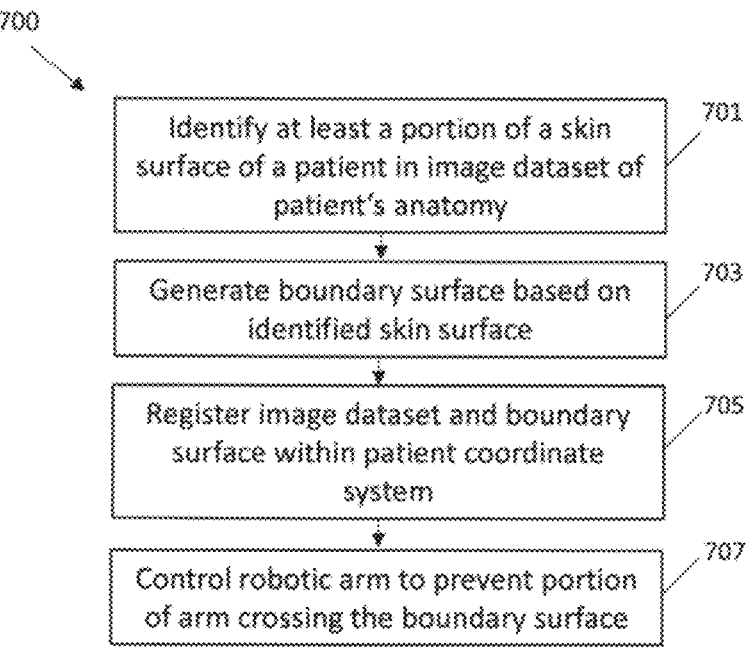
FIG. 7 is a process flow diagram illustrating an embodiment method for defining a three-dimensional boundary surface into which a robotic arm may not enter.

Further embodiments include methods for defining a three-dimensional boundary surface into which the robotic arm 101 may not enter. The boundary surface may correspond to the position of the patient 200 in three-dimensional space and may prevent the robotic arm 101 or any portion thereof, from colliding with the patient 200. FIG. 7 is a process flow diagram that illustrates a method 700 for avoiding patient collisions in a surgical robotic system. The method 700 of FIG. 7 may be implemented using one or more computing devices, such as computer 113 shown in FIG. 1.

In block 701 of method 700, at least a portion of the skin surface of the patient may be identified in an image dataset of the patient's anatomy. The image dataset of the patient's anatomy may be obtained using an imaging device, such as the imaging device 103 shown in FIGS. 1 and 2. The image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The image dataset may be stored electronically in a memory. The image dataset may be in any suitable format, such as in a file format that conforms to the Digital Imaging and Communications in Medicine (DICOM) standard.

In embodiments, the image dataset of the patient's anatomy may be obtained using an imaging device 103 having a relatively wide field-of-view to enable imaging of both the portion of the patient's anatomy requiring surgical intervention and at least a portion of the surrounding skin surface of the patient. For example, where the image dataset comprises a CT dataset, the reconstruction volume may have a diameter that is greater than about 20 cm, such as 50 cm or more, and may extend axially (i.e., along the length of the patient 200) at least about 15 cm, including more than 30 cm, and may extend up to about 1 m or more. In some embodiments, the image dataset may encompass at least about 20%, such as 30-100% (e.g., at least 50%) of the skin surface of the patient extending circumferentially around the portion of the patient's anatomy requiring surgical intervention. The image dataset may additionally encompass at least about 15 cm of skin surface extending in the axial direction.

In embodiments, the at least a portion of the skin surface of the patient 200 may be identified by applying an image segmentation process to the image dataset. Such processes are commonly used in medical imaging to differentiate different tissue types or other anatomic features in image data. Identifying the skin surface may include, for example, performing a thresholding operation on the collected image dataset. In the case of x-ray image data, the thresholding operation may include utilizing an algorithm to analyze the radiodensity values (e.g., Hounsfield units) associated with individual pixels/voxels in the image dataset and based on the analysis, identifying the pixels/voxels within the image data corresponding to the skin surface of the patient 200. Other techniques may also be utilized. As illustrated in FIG. 5A, for example, the patient's skin surface 511 may be clearly differentiated within the displayed x-ray CT data.

In block 703 of method 700, a boundary surface may be generated based on the identified skin surface of the patient 200. The boundary surface may correspond directly with the skin surface identified within the image data or may be a "virtual" three-dimensional surface that may be offset from the actual skin surface by some amount (e.g., 0-2 cm). In some embodiments, a portion of the boundary surface may be generated by extrapolating from the image data. For example, the boundary surface may include a first portion that substantially corresponds to the three-dimensional contour of the portion of the patient's skin surface that is identifiable from the image dataset. The boundary surface may also include a second portion that may be extrapolated beyond the portion of the patient's skin surface that is directly identifiable from the image dataset. In one embodiment, the extrapolated second portion may extend in one or more directions (e.g., axially and/or laterally with respect to the patient) from the first portion and may be based on a modeling of the patient size/shape, where such modeling may be based on empirical or statistical data regarding patient sizes and may be based on patient-specific data (e.g., height, weight, sex, etc.) as well as the dimension(s) of the patient's skin surface that is identifiable from the image dataset. Alternately, the extrapolated second portion may comprise a planar surface that may extend parallel to the surface (e.g., patient table 60) on which the patient 200 is supported. The planar surface may extend at a height above the support surface that is based on the portion of the skin surface identified from the image dataset. For example, the planar surface may extend at a height above the patient support that is equal to the height of the highest portion of the identified skin surface.

In some embodiments, the boundary surface may be generated to encompass one or more objects that extend above the skin surface of the patient. For example, a patient reference marker device 115 may be clamped or otherwise attached to the patient (e.g., to a bony portion of the patient's anatomy) and may include a rigid frame having a plurality of markers affixed thereto that extends above the skin surface. The location of the marker device 115 may be directly identified from the patient image dataset (e.g., via an image segmentation process as described above). Alternately, the marker device 115 may be determined based on the locations of fiducial element(s) (e.g., a set of x-ray opaque elements or beebees) on the marker devices that may be readily identified from the image dataset. The geometric relationship between the fiducial element(s) identified in the image dataset and the outer edges of the marker device 115 extending from the patient may be known, which may enable the generated boundary surface to encompass the marker device 115. This may prevent the robotic arm 101 from colliding with the marker device 115.

In block 705, the image dataset and the boundary surface may be registered within a patient coordinate system. The registration may be performed using a method such as described above with reference to FIG. 3. In particular, the image dataset and the generated boundary surface may be correlated with the patient position which may be determined using a motion tracking system 105 as described above. The image guided surgery system may locate the boundary surface within the patient-centric coordinate system, which may be based on the tracked position of one or more reference marker devices 115 that may be rigidly attached to the anatomical region of interest of the patient 200.

In block 707, a robotic arm may be controlled to prevent any portion of the arm from crossing the boundary surface. In embodiments, this may include executing a control loop that repeatedly reads the joint parameters of the robotic arm while monitoring tracking data indicating the current position and orientation of robotic arm within the patient coordinate system. The position and orientation of the robotic arm may be determined by tracking one or more marker devices (e.g., marker device 202 in FIG. 1) fixed to the robotic arm. The control loop may transform the joint coordinates of the robotic arm into spatial coordinates in the patient coordinate system, and may determine the position of each joint of the arm with respect to the boundary surface. A robotic control system may control the motion of the robotic arm to prevent any portion of the arm from crossing the boundary surface. For example, during motion planning for a particular motion or pose of the robotic arm, the robotic control system may utilize the inverse kinematics of the robotic arm to compute a motion path that avoids crossing the boundary surface. In addition, when operating in a hand guided mode, the robotic control system may brake all or a portion of the robotic arm in order to prevent any portion of the arm from crossing the boundary surface.

Figure 8A:
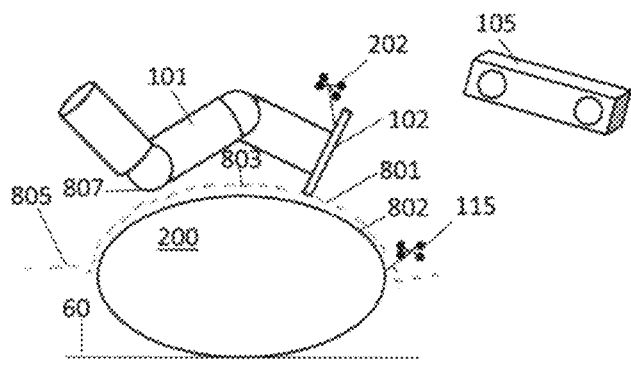
FIG. 8A schematically illustrates a virtual boundary surface over the skin surface of a patient in a surgical robotic system.

FIG. 8A is a schematic cross-section view of a patient 200 and a three-dimensional "virtual" boundary surface 801 extending over at least a portion of the patient. In this embodiment, the boundary surface 801 includes a first portion 803 that corresponds to the three-dimensional contour of the skin surface 802 of the patient 200. In this embodiment, the boundary surface 801 is offset from the skin surface 802, although in other embodiments the boundary surface 801 may coincide with the skin surface 802. A second portion 805 of the boundary surface 801 may be extrapolated from the first portion 803, and in this embodiment includes a planar surface that extends parallel to the patient table 60. A robotic arm 101 may be controlled such that no portion of the robotic arm 101, such as the end effector 102 and joints 807 of the arm 101, may cross the boundary surface 801.

As noted above, the "virtual" boundary surface 801 may be defined within a patient coordinate system that may be based on the tracked position and orientation of the patient marker device 115. The robotic arm 101 may be controlled so as to automatically compensate for any movement of the patient 200 and make suitable movements to maintain the robotic arm 101 outside of the virtual boundary surface 801.

In some embodiments, the robotic arm 101 may be controlled to modify at least one of a velocity, acceleration and torque of the robotic arm 101 as a function of proximity to the boundary surface 801. In particular, as the robotic arm 101 or a portion thereof approaches the boundary surface 801, the robotic control system 405 may reduce the velocity, acceleration and/or torque at one or more joints 807 of the robotic arm 101. This may enable more precise control over the position of the robotic arm 101 vis-a-vis the patient 200 and may provide improved safety in case of accidental contact between the arm 101 and the patient 200.

It will be understood that the method 700 of FIG. 7 is one possible method for defining a boundary surface to prevent a robotic arm from colliding with a patient. Other techniques may be used as an alternative or in addition to the method described above. For example, a user may use a tool or instrument (e.g., a pointer device) that is tracked by the motion tracking system 105 to touch or trace across a set of positions on the patient's skin surface that may be used by the image guided surgery system to generate a boundary surface across which the robotic arm may not enter. A similar method may include operating the robotic arm 101 in a hand guiding mode to trace across a surface that may be then be used to generate a virtual boundary surface. Other methods may include providing a set of marker devices over the skin surface of the patient (e.g., directly on the skin surface or on a surgical drape) and tracking the markers using a motion tracking system. The detected position and orientation of the markers may be extrapolated to define a boundary surface for the robotic arm 101. In addition to defining a boundary surface to avoid patient collisions, these methods may also be used to define boundary surfaces to avoid robot collisions with other potential obstructions, such as the patient table 60, imaging device 103, a cart, tray or other surgical equipment, as well as other individuals (e.g., surgeon(s), scrub nurse(s)) that may be working adjacent to the patient 200.

Figure 8B:
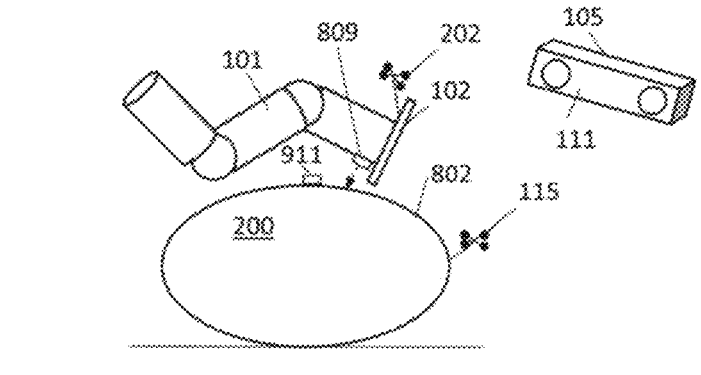
FIG. 8B schematically illustrates a redundant system for avoiding a robotic arm collision with a patient according to an embodiment.

FIG. 8B illustrates an embodiment method and system for preventing a robotic arm 101 from colliding with the patient

200 that includes multiple sensing devices for detecting a patient movement. The sensing devices may utilize multiple different sensing modalities for detecting patient movement. In one embodiment, the first sensing device may be an optical sensing device 111 of a motion tracking system 105 that may receive radiation reflected or emitted from one or more marker devices 115 fixed to the patient 200, as described above. Tracking data from the sensing device 111 may be used to control a robotic arm 101 to prevent the robotic arm 101 from colliding with the patient 200 as described above with reference to FIG. 8A. A second sensing device may be a secondary or redundant sensing device and may help improve the safety of the system such as in the event of a failure or error condition involving the primary sensing device. For example, the motion tracking system 105 may not be able to distinguish between a movement of the patient 200 and a movement of the marker device 115 relative to the patient 200, such as in the event that the marker device 115 becomes loose or is accidentally bumped causing it to change its position/orientation. Similarly, an accidental bumping or movement of the optical sensing device 111 may be erroneously interpreted by the motion tracking system 105 as a movement of the patient 200. In other situations, the motion tracking system 105 may not be able to immediately detect an actual movement of the patient 200, such as if the line of sight between patient marker device 115 and the optical sensing device 111 is temporarily blocked or due to system latency issues. Under such conditions, the robotic arm 101 could accidentally move to a position where it collides with the patient 200.

In the embodiment of FIG. 8B, a second sensing device may include a second optical sensing device 809, such as a LIDAR device or a similar non-contact optically-based system for detecting a distance to a target. Various devices and techniques are known for measuring distance and relative displacement with respect to a target using optical signals, and may be based on, without limitation, triangulation, time-of-flight, interferometry, or confocal chromatic measurement techniques, for example. In some embodiments, the second optical sensing device 809 may be located on the robotic arm 101 and may be configured to detect a distance of the robotic arm 101 from the patient 200.

In some embodiments, a processor (e.g., computer 113 in FIG. 1) may compare a distance between the robotic arm 101 and the patient 200 measured by the second sensing device 809 with the expected distance between the robotic arm 101 and the patient 200 according to the first sensing device (e.g., the motion tracking system 105). Where the distances do not agree with one another by more than a threshold amount, this may indicate that the tracking data from the motion tracking system 105 is not accurate. In response to determining that the distances do not agree by more than a threshold amount, the processor may send a signal to the robotic control system 405 to take a remedial action. The remedial action may include, for example, immediately stopping all current/planned movements of the robotic arm 101, "braking" the robotic arm 101 to prevent hand guiding of the robotic arm 101, triggering an audible and/or visual alarm, controlling the robotic arm 101 to move away from the patient/surgical area, such as by moving the robotic arm 101 to maintain a minimum separation distance from the patient 200 as measured by the second sensing device 809 or by moving the robotic arm 101 to a predetermined "home" pose where it is unlikely to contact the patient 200 or other obstructions, and/or entering a "compliant" mode in which the robotic arm 101 may support its own weight but may otherwise be highly-sensitive and responsive to an applied force by moving the robot in the direction of the applied force.

In other embodiments, the processor may determine whether the distance between the robotic arm 101 and the patient 200 measured by the second sensing device 809 is less than a threshold amount, and may send a signal to the robotic control system 405 to take a remedial action when the measured distance is less than the threshold. The threshold distance may be a default parameter or a user-adjustable parameter. In some embodiments, the threshold distance may be equal to or less than an offset distance between the skin surface 802 and a pre-defined "virtual" boundary surface 801 as described with reference to FIG. 8A. When the measured distance from the second sensing device 809 is less than the threshold distance, this may indicate that the robotic arm 101 has crossed the "virtual" boundary surface 801, and appropriate remedial action may be taken.

In further embodiments, the processor may determine whether the patient 200 and robotic arm 101 are moving toward one another by greater than a pre-determined velocity or acceleration based on data from the second sending device 809, and may take appropriate remedial action in response to such a determination.

In addition to an optical sensor as described above, the second sensing device 809 can include any type of sensing device for monitoring the distance between the robotic arm 101 and the patient 200. The second sensing device 809 may include, for example, magnetic- or RF-based sensors, computer vision systems, capacitive sensors, and/or acoustic (e.g., ultrasonic) sensors.

In one embodiment, a second sensing device may include one or more inertial sensors 911, such as an accelerometer, that may be provided on the patient 200. The one or more inertial sensors 911 may be configured to detect a movement of the patient 200 relative to the robotic arm 101. Where the detected movement does not agree with the tracking data as determined by the motion tracking system 105, a signal may be sent to the robotic control system 405 to take one or more remedial actions as described above.

In further embodiments, the motion tracking system 105 may include a plurality of marker devices 115 attached to the patient 200, such as described in U.S. application Ser. No. 15/701,063 filed on Sep. 11, 2017 ("the '063 Application"), which was previously incorporated by reference herein. As discussed in the '063 Application, the motion tracking system 105 may detect relative movement of the marker devices 115 which may indicate that one or more of the marker devices 115 may have been bumped or become loose and that the patient registration may have become inaccurate. In embodiments, in response to the motion tracking system 105 detecting a relative movement between the marker devices 115 that exceeds a threshold amount, signal may be sent to the robotic control system 405 to take a remedial action as described above.

Figure 8C:
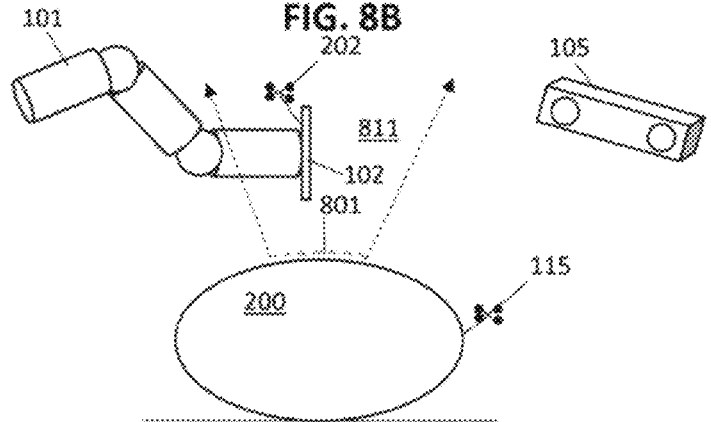
FIG. 8C schematically illustrates a method for defining a virtual three-dimensional volume above a surgical area for controlling an operating mode of a robotic arm.

FIG. 8C illustrates a method of controlling a robotic arm in a surgical robotic system based on a location of the robotic arm relative to a patient. As shown in FIG. 8C, a virtual three-dimensional volume 811 may be defined over the surgical area of the patient 200 within the patient coordinate system of an image guided surgery system. One surface of the volume 811 may comprise a boundary surface 801 over the skin surface of the patient 200 through which the robotic arm 101 may not enter. The boundary surface 801 may be defined using any method, such as the methods described above. The virtual volume 811 may extend from the boundary surface 801 away from the patient 200. The virtual volume 811 may have any size and shape, and may have, for example, a generally cylindrical, cuboid, conical, pyramidal or irregular shape.

The position of the robotic arm 101 may be tracked to determine whether or not a portion of the robotic arm 101 is located within the virtual volume 811. In embodiments, this may include executing a control loop that repeatedly reads the joint parameters of the robotic arm while monitoring tracking data indicating the current position and orientation of robotic arm within the patient coordinate system. The position and orientation of the robotic arm may be determined by tracking one or more marker devices 202 fixed to the robotic arm. The control loop may transform the joint coordinates of the robotic arm into spatial coordinates in the patient coordinate system, and may determine the position of each joint of the arm with respect to the boundaries of the virtual volume 811. In some embodiments, the determination may be whether a particular portion of the robotic arm 101, such as the end effector 102, is inside the virtual volume 811. In other embodiments, the determination may be whether any portion of the robotic arm 101 is located inside the virtual volume 811, or whether every portion of the robotic arm 101 is located inside the virtual volume 811.

An operating mode of the robotic arm 101 may be modified based on the determination of whether a portion of the robotic arm 101 is inside the virtual volume 811. For example, in one embodiment, the control system 405 of the robotic arm 101 may not enable autonomous motion of the robotic arm 101 unless it is determined that at least a portion of the robotic arm 101 (e.g., the end effector 102) is located within the virtual volume 811 above the patient surgical area. In embodiments, the control system 405 may enable hand guided motion of the robotic arm 101 when the arm is both inside and outside of the virtual volume 811. Limiting autonomous movement of the robotic arm 101 to when at least a portion of the robotic arm 101 is inside the virtual volume 811 may help improve safety of the system by minimizing the possibility that the robotic arm 101 could collide with medical personnel or other obstructions in the surgical theater. In embodiments, the robotic arm 101 may first be moved by hand guiding to a position inside the virtual volume 811, and autonomous motions, such as moving the robotic arm 101 to pre-defined trajectories or target locations in a surgical procedure, may be enabled only after the robotic arm 101 is moved into the virtual volume 811. An indicator, which may be provided on a display device 119, 401 or on the robotic arm 101 itself (e.g., an LED indicator), may indicate the position of the robotic arm 101 with respect to the virtual volume 811.

In embodiments, the dimensions and/or shape of the virtual volume 811 may be adjustable by the user. The user may adjust the dimensions and/or shape of the virtual volume 811 based on the position(s) of potential obstruction (s) that the robotic arm 101 could collide with during surgery, including the preferred positions and work areas of medical personnel during surgery.

Figure 9:
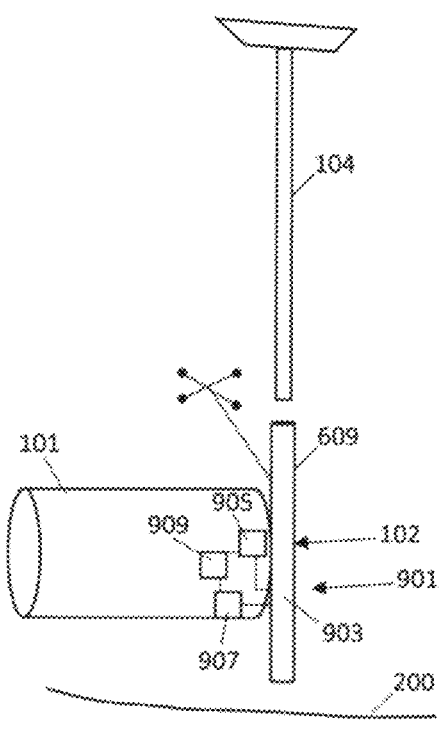
FIG. 9 illustrates a system for detecting the presence of an invasive surgical tool within an end effector of a robotic arm.

Further embodiments include controlling the operation of a robotic arm 101 based on the presence of a tool 104 within an end effector 102 of the robotic arm 101. As discussed above, the end effector 102 of the robotic arm 101 may include a hollow tube or cannula 609 that may be configured to hold one or more tools 104, such as a surgical instrument. The cannula 609 may be used to guide the tool 104 as it is inserted into the patient's body. As shown in FIG. 9, the cannula 609 of the end effector 102 may include a detector device 901 that is configured to detect when a tool 104 is located within the cannula 609.

In one embodiment, the detector device 901 may include an induction coil 903 located in the cannula 609 that is coupled to an AC power source 905, an induction monitoring circuit 907 and a control circuit 909 (e.g., a microprocessor). The induction coil 903 may surround the opening of the cannula 609 so as to enable a tool 104 to be passed through the induction coil 903. In an embodiment, the control circuit 909 may selectively connect the induction coil 903 to the AC power source 905 to induce a magnetic field on the induction coil 903. The inductance monitoring circuit 907 may measure the inductance of the induction coil 903 and communicate the measured inductance to the control circuit 909. The control circuit 909 may determine whether a tool 104 is located within the cannula 609 based on the measured inductance. In one embodiment, the determination may be based on a relative change in the measured inductance from a baseline inductance value which may be measured when no tool 104 is located within the cannula 609. A relative change in the measured inductance that is higher than a threshold value may indicate that a tool 104 is located within the cannula 609. In some embodiments, the detector device 901 may be calibrated to provide an estimated position of a tool 104 within the cannula 609 based on the measured inductance values. The detector device 901 may determine that the tool 104 has been inserted through the entire length of the cannula 609 and thus a portion of the tool 104 may be inside of the patient 200.

The control circuit 909 may send a signal to the robotic control system 405 (see FIG. 4) indicating that a tool 104 is detected within the cannula 609. In response, the robotic control system 405 may control the robotic arm 101 to prevent the robotic arm 101 from moving relative to the patient 200. This may improve the safety of the system by preventing motion of the robotic arm 101 and cannula 609 while an instrument is inserted through the cannula 609 and into the body of the patient 200. In some embodiments, the robotic control system 405 may prohibit certain movements of the robotic arm 101, such as any movement in a direction that is transverse to the trajectory defined by the cannula 609, but may enable movement of the robotic arm 101 along the trajectory. The robotic control system 405 may resume normal operation of the robotic arm 101 upon receiving another signal from the control circuit 909 indicating that the tool 104 has been removed from the cannula 609.

In embodiments in which the robotic arm 101 is mounted to or above an imaging system 103 and may move relative to the patient 200 in conjunction with a movement of at least a portion of the imaging system 103, the control circuit 909 may also send a signal to the imaging system 103 to prevent movement of the system 103 relative to the patient 200 while a tool 104 is detected within the cannula 609.

It will be understood that a detector device 901 including an induction coil 903 is one technique for detecting the presence of a tool 104 within the cannula 609. In other embodiments, the detector device 901 may utilize other mechanisms for detecting the presence of a tool 104 within the cannula 609, such as a pressure sensor, an optical sensor, a capacitive sensor, an acoustic sensor, and/or a mechanical switch.

Further embodiments include methods for defining a virtual surface outside of the patient's body that corresponds to a surface of an anatomical feature located within the patient's body. In embodiments, the virtual surface may be a three-dimensional surface that is defined within the patient coordinate system of an image guided surgery system. A robotic arm 101 may be controlled to provide haptic feedback to a user as the user moves a portion of the robotic arm 101, such as the tip end of an end effector 102 of the robotic arm 101, over the virtual three-dimensional surface.

Figure 10:
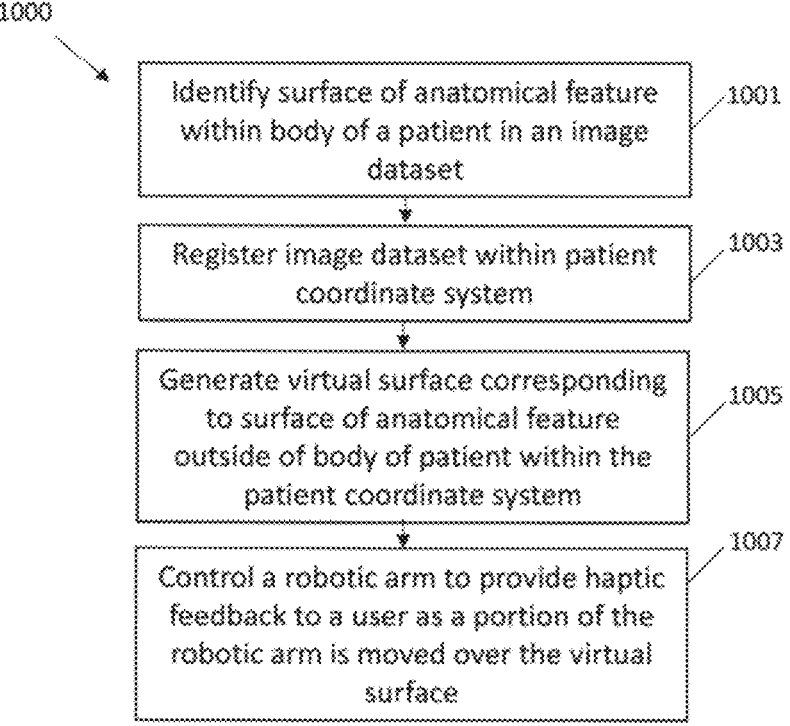
FIG. 10 is a process flow diagram illustrating a method for defining a virtual surface outside of the patient corresponding to a surface of an anatomic feature within the patient in a surgical robotic system.

FIG. 10 is a process flow diagram that illustrates a method 1000 for defining a virtual surface in a surgical robotic system. The method 1000 of FIG. 10 may be implemented using one or more computing devices, such as computer 113 shown in FIG. 1. In block 1001 of method 700, a surface of an anatomical feature within the body of the patient may be identified in an image dataset of the patient's anatomy. The image dataset of the patient's anatomy may be obtained using an imaging device, such as the imaging device 103 shown in FIGS. 1 and 2. The image dataset may be a three-dimensional dataset (e.g., a 3D CT tomographic reconstruction, a 3D MRI dataset, etc.) representing at least a portion of the patient's anatomy, including the internal anatomy and/or structure(s) that are to be operated on (i.e., a surgically-relevant portion of the patient's anatomy). The image dataset may be stored electronically in a memory. The image dataset may be in any suitable format, such as in a file format that conforms to the Digital Imaging and Communications in Medicine (DICOM) standard.

In embodiments, the anatomical feature within the body of the patient may comprise a bone or skeletal feature, such as at least a portion of a spine of the patient. In other embodiments, the anatomical feature may be an internal organ or tissue portion, including an abnormal portion of tissue, such as a tumor. The surface of the anatomical feature may be identified by applying an image segmentation process to the image dataset. In the case of x-ray image data, for example, this may include calibrating radiodensity values (e.g., Hounsfield units) associated with different tissue types (e.g., bone vs. soft tissue) and applying a thresholding algorithm to the image dataset to identify transition points between a tissue type of interest and the surrounding anatomy. As illustrated in FIG. 5B, for example, the surface of the patient's spine 513 may be clearly differentiated within the displayed x-ray CT data. A three-dimensional surface corresponding to the surface of the anatomical feature of interest may be identified within the image dataset.

In block 1003, the image dataset may be registered within a patient coordinate system. The registration may be performed using a method such as described above with reference to FIG. 3. In particular, the image dataset may be correlated with the patient position which may be determined using a motion tracking system 105 as described above.

Figure 11:
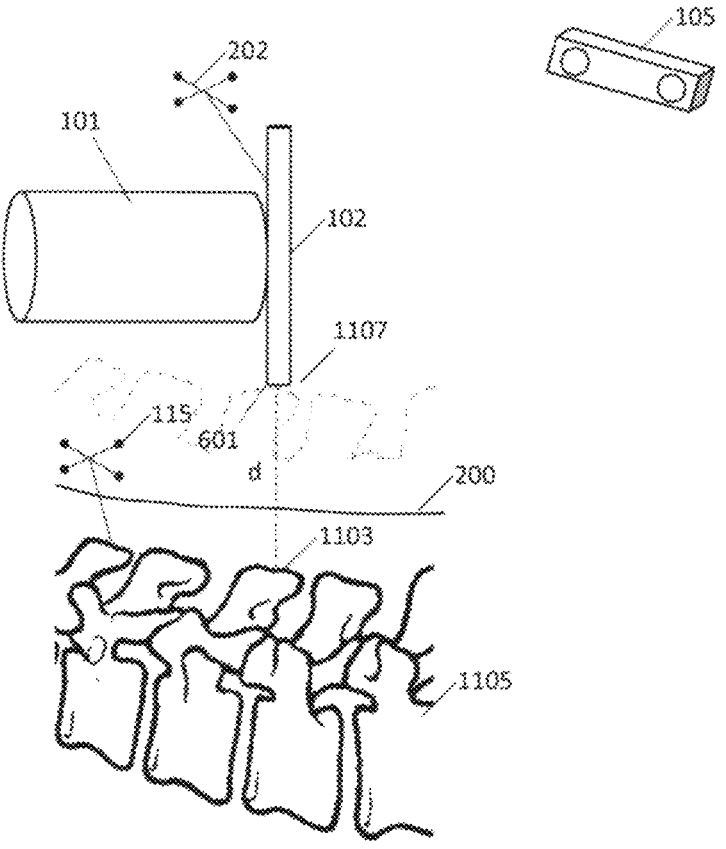
FIG. 11 schematically illustrates an anatomic feature within the body of a patient and the corresponding virtual surface located outside of the patient.

In block 1005, a virtual three-dimensional surface corresponding to the surface of the anatomical feature of the patient may be generated outside of the body of the patient within the patient coordinate system. Generating the virtual three-dimensional surface may include displacing or projecting the surface of the anatomic feature identified within the image dataset to a second location that is outside of the body of the patient 200. This is illustrated in FIG. 11, which schematically shows the surface 1103 of an anatomic feature 1105 (e.g., a portion of a spine) within the body of a patient 200 displaced by a distance d to provide a "virtual" surface 1107 outside of the patient 200. The distance d may be a user-adjustable parameter. The "virtual" surface 1107 may be located within a patient coordinate system of an image guided surgery system. As discussed above, the patient coordinate system may be based on the tracked position of one or more reference marker devices 115 that may be rigidly attached to the anatomical region of interest of the patient 200. The "virtual" surface 1107 may move in conjunction with any movement of the patient 200.

In block 1007 of method 1000, a robotic arm may be controlled to provide haptic feedback to the user as a portion of the robotic arm is moved over the virtual surface 1107. The portion of the robotic arm 101 that is moved over the virtual surface 1107 may be the tip end 601 of an end effector 102, as is illustrated in FIG. 11. In embodiments, controlling the robotic arm 101 may include executing a control loop that repeatedly reads the joint parameters of the robotic arm while monitoring tracking data indicating the current position and orientation of end effector 102 within the patient coordinate system. The position and orientation of the end effector 102 within the patient coordinate system may be determined by tracking one or more marker devices (e.g., marker device 202 in FIG. 11) on the robotic arm 101 relative to a patient reference marker device 115. A robotic control system may control the operation of the robotic arm 101 to provide haptic feedback to the user as the user moves the tip end 601 of the end effector 102 (i.e., in a hand guiding mode) over the virtual surface 1107. In some embodiments, the robotic arm 101 may be controlled to provide increased resistance and/or a vibration of the arm as the user pushes the end effector 102 down against the virtual surface 1107. In some embodiments, the robotic arm 101 may modify the orientation of the end effector 102 such that the tip end 601 of the end effector 102 may "trace" over the contour of the virtual surface 1107 as the end effector 102 is moved laterally over the surface 1107 (e.g., via hand guiding or autonomous robot motion). In some embodiments, the angle of the end effector 102 with respect to the virtual surface 1107 may remain constant as the tip end 601 "traces" over three-dimensional contour of the virtual surface 1107.

Various embodiments of the above-described method 1000 may enable a user (e.g., surgeon) to virtually and non-invasively perceive the contour of the internal anatomical feature of interest while moving the robotic arm 101 outside of the body of the patient 200. Embodiments may provide the user with tactile feedback of the patient's internal anatomy and may assist in planning for a surgical procedure. For example, the surgeon may manipulate the robotic arm 101 over the virtual surface 1107 to determine whether particular portions of the patient's anatomy have a flat, curved or angled surface. In some embodiments, haptic feedback provided by the robotic arm 101 may be calibrated to simulate physical characteristics (e.g., rigidity, compliance, elasticity, etc.) of the underlying anatomic feature.

In embodiments, the user may select a "virtual" trajectory or target location based on the position and/or orientation of the end effector 102 with respect to the virtual surface 1107. In response to the selection of a "virtual" trajectory or target location, the image guided surgery system may set the corresponding trajectory and/or target location within the body of the patient 200. The robotic arm 101 may then be controlled to move to the pre-set trajectories and/or over the target locations inside the patient's body.

Figure 12A:
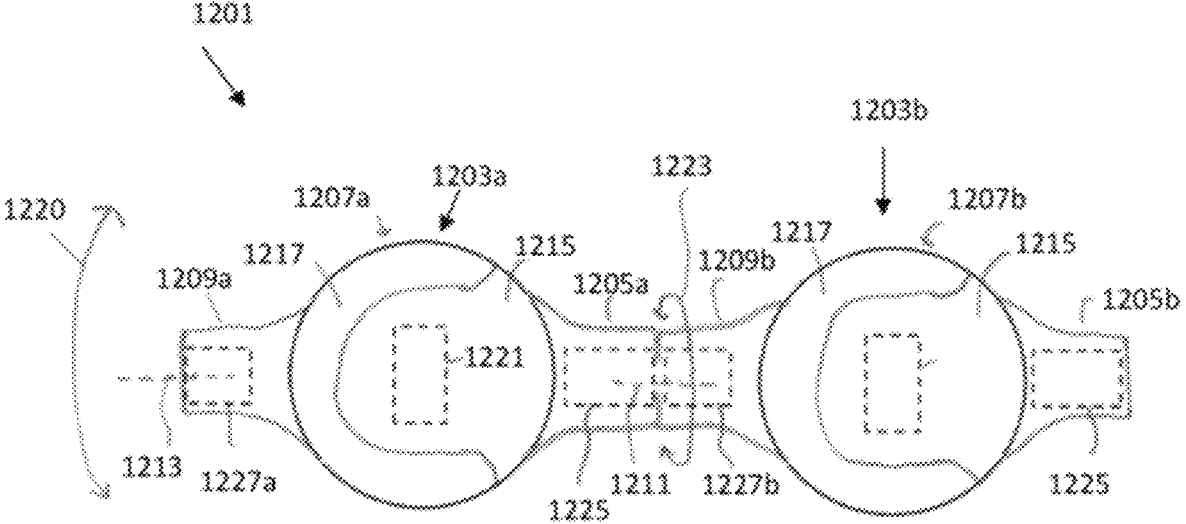
FIGS. 12A-12C illustrate a robotic arm according to an embodiment.
Figures 12B, 12C:
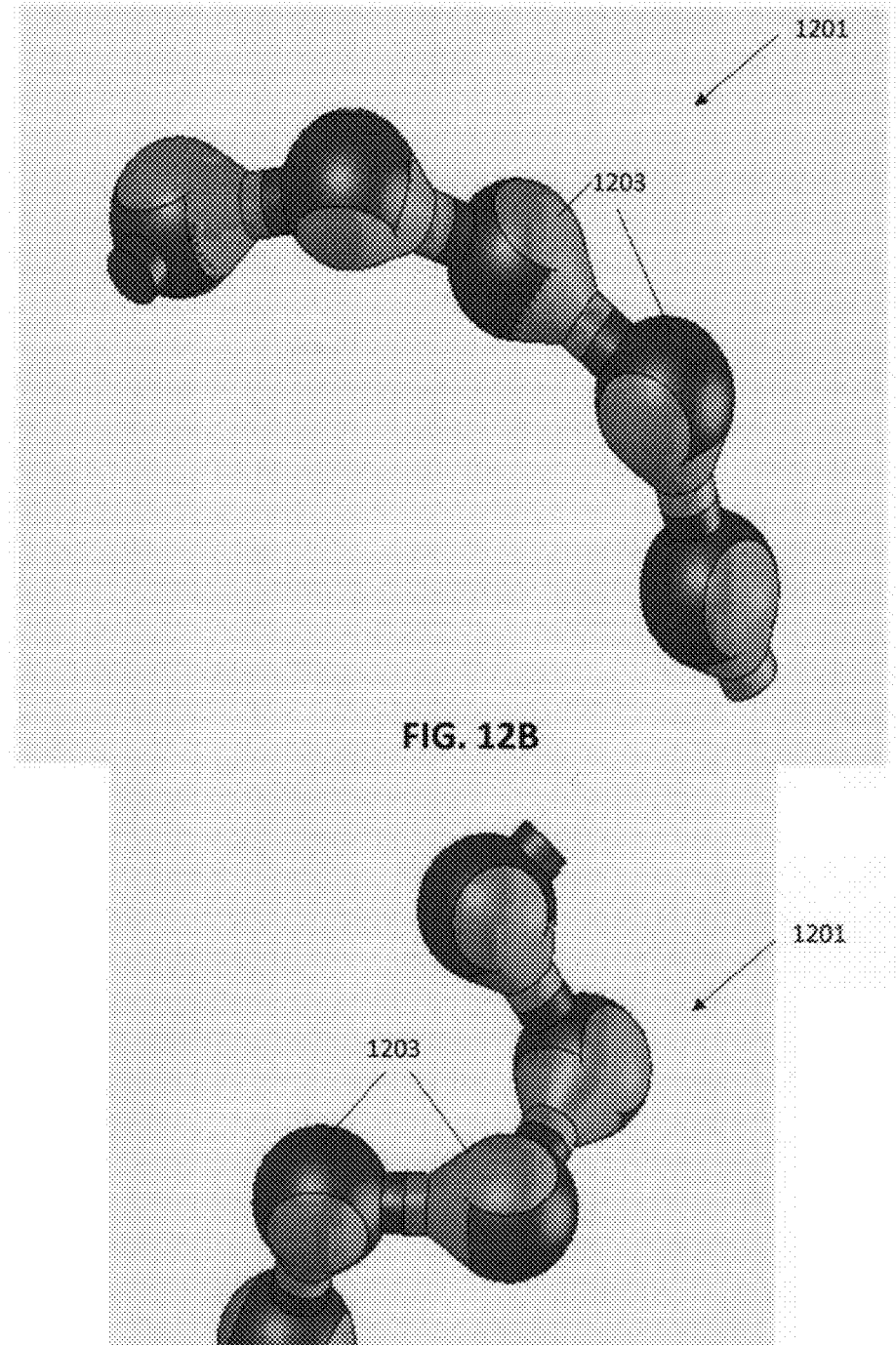

FIGS. 12A-12C illustrate a robotic arm 1201 according to one embodiment. A robotic arm 1201 as shown in FIGS. 12A-12C may be utilized in any of the embodiment methods and systems described herein. It will be understood that other types of robotic arms may also be utilized in the above-described systems and methods.

FIG. 12A is a schematic side view of a robotic arm 1201 according to an embodiment. The robotic arm 1201 may include a plurality of repeating segments 1203a, 1203b that may be coupled end-to-end. Two segments 1203a, 1203b are shown in FIG. 12A. A robotic arm 1201 according to various embodiments may include any number of segments, such as 2, 3, 4, 5, 6 segments or more.

Each segment 1203a, 1203b may include a first end portion 1205a, 1205b, a second end portion 1209a, 1209b, and a central portion 1207a, 1207b having a generally spheroid-shaped outer surface, such as a truncated sphere shape. The first and second end portions 1205, 1209 may have a smaller outer diameter than the generally spheroid-shaped central portion 1207. The first and second end portions 1205, 1209 may have a curved outer surface and may be generally cylindrically-shaped. In embodiments, the end portions 1205, 1209 may have a tapered diameter extending away from the central portion 1207, as shown in FIG. 12A.

The robotic arm 1201 as shown in FIG. 12A may have a rounded outer surface with smooth transitions and may be free of sharp corners or edges that could tear a sterile covering, such as a surgical drape, provided over the robotic arm 1201. The robotic arm 1201 may be particularly advantageous for use in robot assisted surgery.

Adjacent segments 1203a, 1203b may be coupled along an axis 1211, as shown in FIG. 12A. The axis 1211 may extend longitudinally through the first end portion 1205a of segment 1203a and the second end portion 1209b of the adjacent segment 1203b. Each segment 1203a, 1203b may provide at least two rotational degrees of freedom such that a second axis 1213 extending longitudinally through second end portion 1209a of the segment 1203a may rotate in two mutually perpendicular directions with respect to axis 1211. As shown in FIG. 12A, for example, axis 1213 may rotate in the pitch direction (i.e., up and down within the plane of the page in FIG. 12A) and in the yaw direction (i.e., into and out of the page in FIG. 12A) with respect to axis 1211. In embodiments, axis 1213 may rotate at least about ±15 degrees, such as ±20 degrees, ±30 degrees, ±45 degrees and ±100 degrees or more, with respect to axis 1211 in the pitch and yaw directions. The second end portion 1209a of segment 1203a may be coupled to an additional segment 1203 of the robotic arm 1201, or where segment 1203a is the final segment of the arm 1201, to an end effector of the robotic arm 1201.

In the embodiment of FIG. 12A, the central portion 1207 of each segment 1203 may include a pair of nested spherical portions, including an outer spherical portion 1215 coupled to the first end portion 1205 and an inner spherical portion 1217 coupled to the second end portion 1209. The inner spherical portion 1217 and second end portion 1209 may be rotatable with respect to the outer spherical portion 1215 and first end portion 1205 in the direction of arrow 1220. A motor 1221 located within the central portion 1207 may drive the rotation of the inner spherical portion 1217 relative to the outer spherical portion 1215. An encoder (not illustrated) within the central portion 1207 may determine the rotational position of the inner spherical portion 1217 relative to the outer spherical portion 1215.

In addition, in the embodiment of FIG. 12A the first end portion 1205a of segment 1203a may be coupled to the second end portion 1209b of the adjacent segment 1203b via a rotary bearing that enables segment 1203a to rotate with respect to segment 1203b in the direction of arrow 1223. A motor 1225 may be located in the first end portion 1205a to drive the rotation of segment 1203a with respect to segment 1203b. An encoder (not illustrated) may determine the rotational position of the first end portion 1205a of segment 1203a relative to the second end portion 1209b of segment 1203b.

Motors 1225 and 1221 may be controlled to provide coordinated motion of the segment 1203a in the directions of arrows 1223 and 1220. In the embodiment of FIG. 12A, a rotation of the second end portion 1209 in the direction of arrow 1220 in conjunction with a rotation of the entire segment 1203 in the direction of arrow 1223 may provide pitch and yaw rotation of the second end portion 1209 with respect to axis 1211.

The different segments 1203 of the robotic arm 1201 may be connected in a daisy-chain configuration such that power and data (e.g., control signals) may be passed down sequentially through each segment 1203 of the arm 1201 and data (e.g., encoder data) may be passed back through the segments 1203 to a robotic control system. Slip rings 1227*a*, 1227*b*, which may be located on the second end portions 1209*a*, 1209*b* of the segments 1203*a*, 1203*b* may be used to pass power and data between the segments 1203*a*, 1203*b*. This configuration may enable continuous (i.e., >360°) rotation between adjacent segments in the direction of arrow 1223.

In embodiments, each segment 1203 may include an inertial sensor (e.g., accelerometer) that may be used for dynamic gravity calibration at each segment 1203 (e.g., without having to input the gravity vector at the robot base). The inertial sensor may also be used for redundant motion control (e.g., in addition to the encoders in each segment 1203).

FIGS. 12B and 12C illustrate a robotic arm 1201 that includes five segments 1203 moved to different poses. In embodiments, the robotic arm 1201 may be curled up into relative tight configurations and radii without reaching joint limits. For example, the robotic arm 1201 may be able to reach into and/or through the bore 107 of an imaging system 103. The robotic arm 1201 may also be controlled to approach a patient 200 in a relatively smooth arc, such as shown in FIG. 12B. The robotic arm 1201 may be controlled such that the arc is directed upwards away from the patient 200. Moving the end effector of the robotic arm 1201 towards and away from the base end of the arm may be achieved by changing the radius of the arc.

Figure 13:
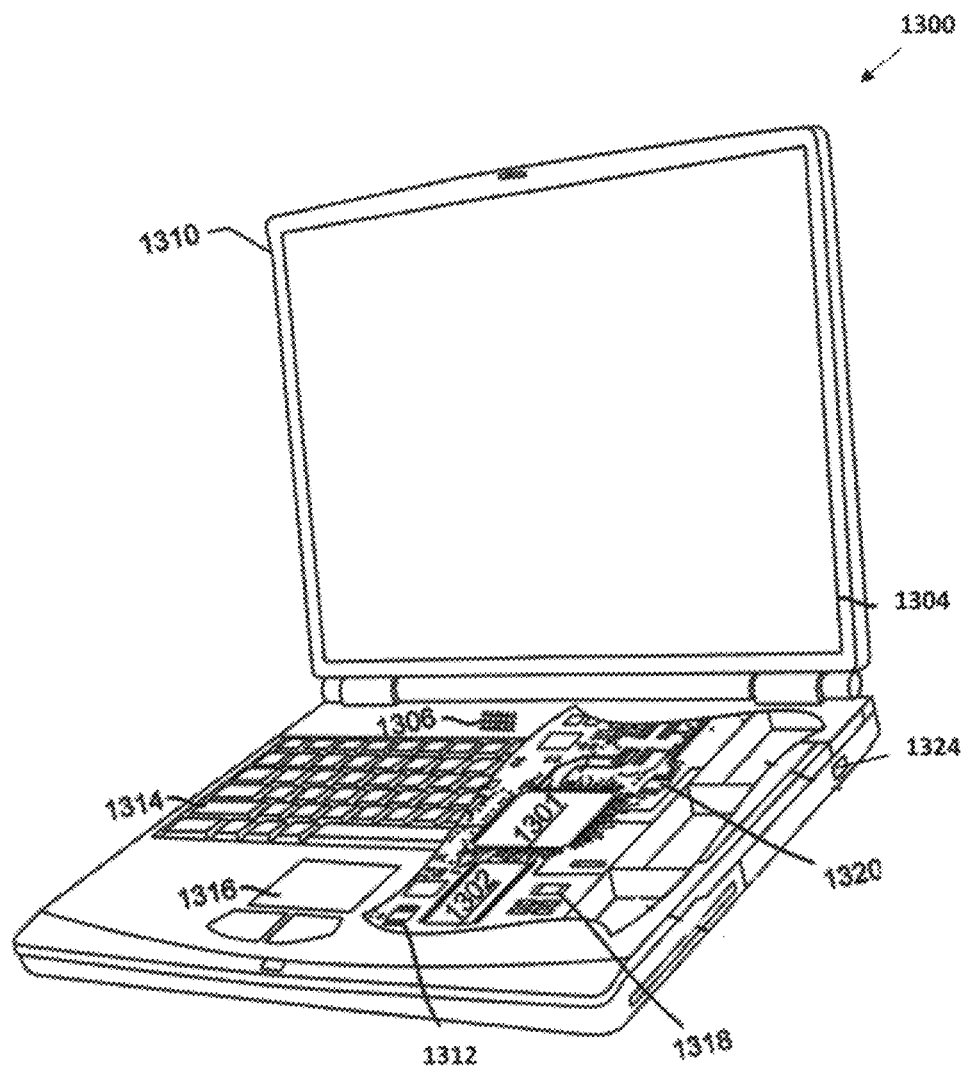
FIG. 13 schematically illustrates a computing device which may be used for performing various embodiments.

FIG. 13 is a system block diagram of a computing device 1300 useful for performing and implementing the various embodiments described above. The computing device 1300 may perform the functions of an image guided surgery system 400 and/or a robotic control system 405, for example. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a non-volatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A method for preventing a robotic arm from colliding with a patient, comprising:

tracking at least one of a position and orientation of a robotic arm with an end effector relative to a patient using a motion tracking system, the end effector including a cannula configured to allow one or more instruments to removably pass through the cannula below an epidermal surface of the patient;

tracking a position and an orientation of the patient with one or more patient markers with the motion tracking system;

generating a boundary surface based on identifying at least a portion of the epidermal surface of the patient, wherein the boundary surface comprises a virtual three-dimensional surface above the epidermal surface of the patient;

preventing the end effector from crossing the boundary surface;

detecting the position of the patient relative to the robotic arm; and controlling the robotic arm to take a remedial action based on the position of the patient relative to the robotic arm.

2. The method of claim 1, wherein the boundary surface is offset from the epidermal surface by a predetermined amount.

3. The method of claim 1, further comprising registering an image dataset and the boundary surface within a patient coordinate system.

4. The method of claim 3, wherein the robotic arm executes a control loop that repeatedly reads joint parameters of the robotic arm while monitoring tracking data of the patient from the motion tracking system indicating a current position and orientation of the robotic arm within the patient coordinate system.

5. The method of claim 1, wherein end effector is controlled to be prevented from crossing the boundary surface by modifying at least one of a velocity, acceleration, and torque of the robotic arm as a function of proximity to the boundary surface.

6. The method of claim 1, further comprising identifying the at least a portion of the epidermal surface of the patient in an image dataset of an anatomy of the patient, wherein the image dataset comprises at least one of a three-dimensional x-ray CT reconstruction and a three-dimensional MRI dataset.

7. The method of claim 1, further comprising defining a target location below the epidermal surface of the patient.

8. The method of claim 7, further comprising maintaining the end effector of the robotic arm pointed along a trajectory intersecting with the target location.

9. The method of claim 8, further comprising allowing movement of the robotic arm to advance the end effector along the trajectory toward the target location.

10. The method of claim 9, wherein the cannula is further defined as being configured to allow one or more instruments to removably pass through the cannula to the target location along the trajectory.

11. The method of claim 1, wherein the remedial action comprises at least one of: immediately stopping all current and/or planned movements of the robotic arm, preventing hand guiding of the robotic arm, triggering an audio and/or visual alarm, controlling the robotic arm to move away from the patient, and entering a compliant mode characterized by an increased sensitivity and/or responsiveness of the robotic arm to an applied force.

* * * * *